US008501918B2

(12) United States Patent
Howell

(10) Patent No.: US 8,501,918 B2
(45) Date of Patent: Aug. 6, 2013

(54) IMMOBILIZED TUMOR NECROSIS FACTOR-α MUTEINS FOR ENHANCING IMMUNE RESPONSE IN MAMMALS

(75) Inventor: Mark Douglas Howell, Fort Collins, CO (US)

(73) Assignee: Cytologic, Inc., Boulder, CO (US)

( * ) Notice: Subject to any disclaimer, the term of this patent is extended or adjusted under 35 U.S.C. 154(b) by 0 days.

(21) Appl. No.: 12/378,078

(22) Filed: Feb. 11, 2009

(65) Prior Publication Data

US 2009/0227750 A1 Sep. 10, 2009

Related U.S. Application Data

(63) Continuation of application No. 11/234,057, filed on Sep. 22, 2005, now abandoned.

(51) Int. Cl.

| | |
|---|---|
| ***C07K 14/525*** | (2006.01) |
| ***C07K 17/02*** | (2006.01) |
| ***C07K 17/12*** | (2006.01) |
| ***C07K 17/14*** | (2006.01) |
| ***A61K 35/14*** | (2006.01) |

(52) U.S. Cl.

USPC ........... 530/413; 530/351; 530/402; 930/144; 604/5.01

(58) Field of Classification Search

None

See application file for complete search history.

(56) References Cited

U.S. PATENT DOCUMENTS

| | | | | |
|---|---|---|---|---|
| 4,116,589 | A | | 9/1978 | Rishton |
| 4,189,470 | A | | 2/1980 | Rose |
| 4,191,182 | A | | 3/1980 | Popovich et al. |
| 4,350,156 | A | | 9/1982 | Malchesky et al. |
| 4,362,155 | A | | 12/1982 | Skurkovich |
| 4,375,414 | A | | 3/1983 | Strahilevitz |
| RE31,688 | E | | 9/1984 | Popovich et al. |
| 4,486,282 | A | | 12/1984 | Bier |
| 4,581,010 | A | | 4/1986 | Skurkovich et al. |
| 4,605,394 | A | | 8/1986 | Skurkovich |
| 4,614,513 | A | | 9/1986 | Bensinger |
| 4,620,977 | A | | 11/1986 | Strahilevitz |
| 4,633,417 | A | | 12/1986 | Wilburn et al. |
| 4,634,417 | A | | 1/1987 | Korec |
| 4,664,913 | A | | 5/1987 | Mielke et al. |
| 4,708,713 | A | | 11/1987 | Lentz |
| 4,801,449 | A | | 1/1989 | Balint, Jr. et al. |
| 4,813,924 | A | | 3/1989 | Strahilevitz |
| 4,824,432 | A | | 4/1989 | Skurkovich et al. |
| 4,834,973 | A | | 5/1989 | Strahilevitz |
| 4,865,841 | A | | 9/1989 | Balint, Jr. et al. |
| 4,877,830 | A | * | 10/1989 | Dobeli et al. ................ 525/54.3 |
| 4,963,265 | A | | 10/1990 | Okarma et al. |
| 5,037,645 | A | | 8/1991 | Strahilevitz |
| 5,037,649 | A | | 8/1991 | Balint, Jr. et al. |
| 5,078,673 | A | | 1/1992 | Abrams |
| 5,135,919 | A | | 8/1992 | Folkman et al. |
| 5,147,638 | A | | 9/1992 | Esmon et al. |
| 5,264,563 | A | | 11/1993 | Huse |
| 5,290,807 | A | | 3/1994 | Folkman et al. |
| 5,356,374 | A | | 10/1994 | Hogan et al. |
| 5,486,463 | A | * | 1/1996 | Lesslauer et al. ............ 435/69.5 |
| 5,523,096 | A | | 6/1996 | Okarma et al. |
| 5,523,388 | A | | 6/1996 | Huse |
| 5,597,899 | A | * | 1/1997 | Banner et al. ................. 530/351 |
| 5,605,690 | A | | 2/1997 | Jacobs et al. |
| 5,626,843 | A | | 5/1997 | Skurkovich et al. |
| 5,629,327 | A | | 5/1997 | D'Amato |
| 5,639,725 | A | | 6/1997 | O'Reilly et al. |
| 5,643,732 | A | | 7/1997 | Strahilevitz |
| 5,679,260 | A | | 10/1997 | Boos et al. |
| 5,698,586 | A | | 12/1997 | Kishimoto et al. |
| 5,705,615 | A | | 1/1998 | Lim et al. |
| 5,712,291 | A | | 1/1998 | D'Amato |
| 5,713,491 | A | | 2/1998 | Hughes et al. |
| 5,716,981 | A | | 2/1998 | Hunter et al. |
| 5,730,713 | A | | 3/1998 | Okarma et al. |
| 5,733,876 | A | | 3/1998 | O'Reilly et al. |
| 5,753,227 | A | | 5/1998 | Strahilevitz |

(Continued)

FOREIGN PATENT DOCUMENTS

| | | | |
|---|---|---|---|
| DE | 3302384 | A1 | 7/1984 |
| EP | 0076665 | A2 | 4/1983 |

(Continued)

OTHER PUBLICATIONS

Sepharose and Sepharose CL Gel Filtration Media, Sigma-Aldrich, St. Louis, Missouri [online], Mar. 2003 [retrieved on May 9, 2012]. Retrieved from the Internet: URL: http://www.sigmaaldrich.com/etc/medialib/docs/Sigma/Product_Information_Sheet/cl6b200pis.Par.0001.File.tmp/cl6b200pis.pdf.*

Zhang et al. Site-directed mutational analysis of human tumor necrosis factor-alpha receptor binding site and structure-functional relationship. J Biol Chem. Nov. 25, 1992;267(33):24069-75.*

Van Hauwermeiren et al. Treatment of TNF mediated diseases by selective inhibition of soluble TNF or TNFR1. Cytokine Growth Factor Rev. Oct.-Dec. 2011;22(5-6):311-9.*

Harlow et al., Antibodies, A Laboratory Manual, Chapter 13, "Immunoaffinity Purification," 1988, pp. 511-552, p. 514.*

Interference Proceedings No. 105,413—relating to Confidential Settlement Agreement and Withdrawal of Appeal (Jul. 2010), 17 pages.

(Continued)

*Primary Examiner* — David Romeo

(74) *Attorney, Agent, or Firm* — Patterson Thuente Pedersen, P.A.

(57) ABSTRACT

The present invention provides a method for enhancing an immune response in a mammal to facilitate the elimination of a chronic pathology. The method involves the removal of immune system inhibitors such as soluble TNF receptor from the circulation of the mammal, thus, enabling a more vigorous immune response to the pathogenic agent. The removal of immune system inhibitors is accomplished by contacting biological fluids of a mammal with one or more binding partner(s) such as TNFα muteins capable of binding to and, thus, depleting the targeted immune system inhibitor(s) from the biological fluids. Particularly useful in the invention is an absorbent matrix composed of an inert, biocompatible substrate joined covalently to a binding partner, such as a TNFα mutein, capable of specifically binding to a targeted immune system inhibitor such as soluble TNF receptor.

13 Claims, 8 Drawing Sheets

U.S. PATENT DOCUMENTS

| | | | |
|---|---|---|---|
| 5,840,588 A | 11/1998 | Strahilevitz | |
| 5,861,483 A | 1/1999 | Wolpe | |
| 5,869,047 A | 2/1999 | Blake | |
| 5,888,511 A | 3/1999 | Skurkovich et al. | |
| 5,910,252 A | 6/1999 | Truitt et al. | |
| 5,919,898 A | 7/1999 | Nakatani et al. | |
| 5,980,887 A | 11/1999 | Isner et al. | |
| 6,017,527 A | 1/2000 | Maraskovsky et al. | |
| 6,039,946 A | 3/2000 | Strahilevitz | |
| RE36,755 E | 6/2000 | Smith et al. | |
| 6,197,289 B1 | 3/2001 | Wirt et al. | |
| 6,221,614 B1 | 4/2001 | Prusiner et al. | |
| 6,231,536 B1 | 5/2001 | Lentz | |
| 6,245,038 B1 | 6/2001 | Borberg et al. | |
| 6,264,623 B1 | 7/2001 | Strahilevitz | |
| 6,287,516 B1 | 9/2001 | Matson et al. | |
| 6,379,708 B1 | 4/2002 | Howell et al. | |
| 6,428,790 B1 | 8/2002 | Boyd | |
| 6,432,405 B1 | 8/2002 | Weinberg et al. | |
| 6,528,057 B1 | 3/2003 | Ambrus et al. | |
| 6,561,997 B1 | 5/2003 | Weitzel et al. | |
| 6,569,112 B2 | 5/2003 | Strahilevitz | |
| 6,602,502 B1 | 8/2003 | Strahilevitz | |
| 6,602,993 B2 | 8/2003 | Wallach et al. | |
| 6,607,501 B2 | 8/2003 | Gorsuch | |
| 6,607,723 B1 | 8/2003 | Good et al. | |
| 6,620,382 B1 | 9/2003 | Lentz | |
| 6,627,151 B1 | 9/2003 | Borberg et al. | |
| 6,630,315 B1 | 10/2003 | Miwa et al. | |
| 6,676,622 B2 | 1/2004 | Strahilevitz | |
| 6,685,664 B2 | 2/2004 | Levin et al. | |
| 7,368,295 B2 * | 5/2008 | Tovar et al. | 436/526 |
| 2001/0010818 A1 | 8/2001 | Engle et al. | |
| 2001/0039392 A1 | 11/2001 | Strahilevitz | |
| 2002/0019603 A1 | 2/2002 | Strahilevitz | |
| 2002/0058031 A1 | 5/2002 | Tung et al. | |
| 2002/0086276 A1 | 7/2002 | Srivastava | |
| 2002/0107469 A1 | 8/2002 | Bolan et al. | |
| 2002/0111577 A1 | 8/2002 | Sirimanne et al. | |
| 2002/0159995 A1 | 10/2002 | Brady et al. | |
| 2002/0183677 A1 | 12/2002 | Chang et al. | |
| 2002/0187069 A1 | 12/2002 | Levin et al. | |
| 2002/0197249 A1 | 12/2002 | Brady et al. | |
| 2002/0197250 A1 | 12/2002 | Brady et al. | |
| 2002/0197251 A1 | 12/2002 | Brady et al. | |
| 2003/0073822 A1 | 4/2003 | Lofling et al. | |
| 2003/0118584 A1 | 6/2003 | Glenn et al. | |
| 2003/0125657 A1 | 7/2003 | Koll et al. | |
| 2003/0127390 A1 | 7/2003 | Davis, Jr. | |
| 2003/0133929 A1 | 7/2003 | Cham | |
| 2003/0138349 A1 | 7/2003 | Robinson et al. | |
| 2003/0148404 A1 | 8/2003 | Michaelson | |
| 2003/0163077 A1 | 8/2003 | Kim et al. | |
| 2003/0195452 A1 | 10/2003 | Hunley et al. | |
| 2003/0215443 A1 | 11/2003 | Coffey et al. | |
| 2004/0044301 A1 | 3/2004 | Levin et al. | |
| 2004/0054315 A1 | 3/2004 | Levin et al. | |

FOREIGN PATENT DOCUMENTS

| | | | |
|---|---|---|---|
| EP | 0184 040 A2 | | 6/1986 |
| EP | 0 619 372 | * | 12/1994 |
| GB | 1562546 | | 3/1980 |
| GB | 2136314 A | | 9/1984 |
| JP | 56092824 | | 7/1981 |
| JP | 2045064 | | 2/1990 |
| WO | WO 79/01121 | | 12/1979 |
| WO | WO 91/09966 | | 7/1991 |
| WO | WO 96/16666 | | 6/1996 |
| WO | WO 03/020320 | * | 3/2003 |
| WO | WO 2007/038386 | | 4/2007 |

OTHER PUBLICATIONS

Abbruzzese et al., "A Phase II Trial of Recombinant Human Interferon-Gamma and Recombinant Tumor Necrosis Factor in Patients with Advanced Gastrointestinal Malignancies: Results of a Trial Terminated by Excessive Toxicity," *Journal of Biological Response Modifiers*, 9(5):522-527 (1990).

Aderka et al., "Increased Serum Levels of Soluble Receptors for Tumor Necrosis Factor in Cancer Patients," *Cancer Research*, 51:5602-5607 (1991).

Adolf et al., A Monoclonal Antibody-Based Enzyme Immunoassay for Quantitation of Human Tumor Necrosis Factor Binding Protein I, A Soluble Fragment of the 60 kDa TNF Receptor, In Biological Fluids, *Journal of Immunoloaical Methods*, 143:127-136 (1991).

Ajani et al., "Phase I and II Studies of the Combination of Recombinant Human Interferon-y and 5-Fluorouracil in Patients with Advanced Colorectal Carcinoma," *Journal of Biological Response Modifiers*, 8(2):140-146 (1989).

Albertini et al., "Limiting Dilution Analysis of Lymphokine-Activated Killer Cell Precursor Frequencies in Peripheral Blood Lymphocytes of Cancer Patients Receiving Interleukin-2 Therapy," *Journal of Biological Response Modifiers*, 9(5):456-462 (1990).

Amit et al., "Three-dimensional structure of an antigen-antibody complex at 2.8 Å resolution," *Science*, 233:747-753 (1986).

Arend, "Inhibiting the Effects of Cytokines in Human Diseases," *Advances in Internal Medicine*, 40:365-394 (1995).

Avner et al., "Therapeutic Murine Monoclonal Antibodies Developed for Individual Cancer Patients," *Journal of Biological Response Modifiers*, 8(1):25-36 (1989).

Balcewicz-Sablinska et al., "Pathogenic *Mycobacterium tuberculosis* Evades Apoptosis of Host Macrophages by Release of TNF-R2, Resulting in Inactivation of TNF- $\alpha^1$ ," *Journal of Immunology*, 161:2636-2641 (1998).

Baliko et al., "Th2 Biased Immune Response in Cases With Active *Mycobacterium tuberculosis* Infection and Tuberculin Anergy," *FEMS Immunology and Medical Microbiology*, 22:199-204 (1998).

Barbara et al., "Dissociation of TNF-α Cytotoxic and Proinflammatory Activities by p55 Receptor- and p75 Receptor-Selective TNF-α Mutants," *EMBO Journal*, 13(4):843-850 (1994).

Bermudez et al., "Infection with *Mycobacterium avium* Induces Production of Interleukin-10 (IL-10), and Administration of Anti-IL-10 Antibody is Associated with Enhanced Resistance to Infection in Mice," *Infection and Immunity*, 61(7):3093-3097 (1993).

Beutler et al., "The Biology of Cachectin/TNF—A Primary Mediator of the Host Response," *Ann. Rev. Immunol.*, 7:625-655 (1989).

Bläuer et al., "Modulation of the Antilisterial Activity of Human Blood-Derived Macrophages by Activating and Deactivating Cytokines," *Journal of Interferon and Cytokine Research*, 15:105-114 (1995).

Boman et al., "Phase I Study of Recombinant Gamma-Interferon (rIFN-γ)," *Journal of Biological Response Modifiers*, 7(5):438-446 (1988).

Bruntsch et al., "Phase II Study of Recombinant Human Interferon-γ in Metastatic Renal Cell Carcinoma," *Journal of Biological Response Modifiers*, 9(3):335-338 (1990).

Bukowski et al., "Phase I Trial of Continuous Infusion Recombinant Interleukin-2 and Intermittent Recombinant Interferon-$\alpha_{2a}$: Clinical Effects," *Journal of Biological Response Modifiers*, 9(6):538-545 (1990).

Caulfield et al., "Phase 1a-1b Trial of an Anti-$G_{D3}$ Monoclonal Antibody in Combination with Interferon-α in Patients with Malignant Melanoma," *Journal of Biological Response Modifiers*, 9(3):319-328 (1990).

Chambrier et al., "Hormonal and Metabolic Effects of Chronic Interleukin-2 Infusion in Cancer Patients," *Journal of Biological Resoonse Modifiers*, 9(2):251-255 (1990).

Chen et al., "Solubie TNF-α Receptors Are Constitutively Shed and Downregulate Adhesion Molecule Expression in Malignant Gliomas," *Journal of Neuropathology and Experimental Neurology*, 56(5):541-550 (1997).

Chouaib et al., "More Insights Into the Complex Physiology of TNF," *Immunology Today*, 12(5):141-142 (1991).

Coclet-Ninin et al., "Interferon-Beta Not Only Inhibits Interleukin-1β and Tumor Necrosis Factor-α but Stimulates Interleukin-1 Receptor Antagonist Production in Human Peripheral Blood Mononuclear Cells," *Eur. Cytokine Network*, 8(4):345-349 (1997).

Colman et al., "Hemostasis and Thrombosis: Basic Principles and Clinical Practice," Chapter 5 (2nd Ed.), p. 60-96, J.B. Liopincott; Philadelohia, PA (1987).

Cox et al., "Phase II Study of Human Lymphoblastoid Interferon in Patients with Multiple Myeloma," *Journal of Biological Response Modifiers*, 7(3):318-325 (1988).

Creaven et al., "Initial Clinical Trial of the Macrophage Activator Muramyl Tripeptide-Phosphatidylethanolamine Encapsulated in Liposomes in Patients with Advanced Cancer," *Journal of Biological Response Modifiers*, 9(5):492-498 (1990).

Croghan et al., "A Phase I Trial of Recombinant Interferon-α and α—Difluoromethylornithine in Metastatic Melanoma," *Journal of Biological Response Modifiers*, 7(4):409-415 (1988).

D'Andrea et al., "Interleukin 10 (IL-10) Inhibits Human Lymphocyte Interferon γ-Production by Suppressing Natural Killer Cell Stimulatory Factor/IL-12 Synthesis in Accessory Cells," *J. Exp. Med.*, 178:1041-1048 (1993).

Digel et al., "High Levels of Circulating Soluble Receptors for Tumor Necrosis Factor in Hairy Cell Leukemia and Type B Chronic Lymphocytic Leukemia," *J. Clin. Invest.*, 89:1690-1693 (1992).

Dimery et al., "Recombinant Interteron-γ in the Treatment of Recurrent Nasopharyngeal Carcinoma," *Journal of Biological Response Modifiers*, 8(3):221-226 (1989).

Dinarello, "Induction of Interleukin-1 and Interleukin-1 Receptor Antagonist," *Seminars in Oncology*, 24(3)(9):S9-81-S9-93 (1997).

Dupere et al., "Patterns of Cytokines Released by Peripheral Blood Leukocytes of Normal Donors and Cancer Patients During Interleukin-2 Activation In Vitro," *Journal of Biological Response Modifiers*, 9(2):140-148 (1990).

Ebach et al., "Opposing effects of tumor necrosis factor receptor 1 and 2 in sepsis due to cecal ligation and puncture", *Shock*, Apr. 2005, 23(4):311-318.

Eck et al., "The Structure of Tumor Necrosis Factor-α at 2.6 Å Resolution," *Journal of Biological Chemistry*, 264(29):17595-17605 (1989).

Elsässer-Beile et al., "Increased Plasma Concentrations for Type I and II Tumor Necrosis Factor Recectors and IL-2 Receptors in Cancer Patients," *Tumor Biology*, 15:17-24 (1994).

Engelhardt et al., "Biological Response to Intravenously Administered Endotoxin in Patients with Advanced Cancer," *Journal of Biological Response Modifiers*, 9(5):480-491 (1990).

Engelmann et al., "Two Tumor Necrosis Factor-binding Proteins Purified from Human Urine," *Journal of Biological Chemistry*, 265(3):1531-1536 (1990).

Eriks et al., "Temporal Effect of Tumor Necrosis Factor Alpha on Murine Macrophages Infected with *Mycobacterium avium*," *Infection and Immunity*, 65(6):2100-2106 (1997).

Etges et al., "Progressive Disease or Protective Immunity to *Leishmania major* Infection: The Result of a Network of Stimulatory and Inhibitory Interactions," *J. Mol. Med.*, 76:372-390 (1998).

Fareed et al., "Novel Antigenic Markers of Human Tumor Regression," *Journal of Biological Response Modifiers*, 7(1):11-23 (1988).

Favrot et al., "Functional and Immunophenotypic Modifications Induced by Interleukin-2 Did Not Predict Response to Therapy in Patients with Renal Cell Carcinoma," *Journal of Biological Response Modifiers*, 9(2):167-177 (1990).

Fernandes et al., "Interleukin-10 Downregulates Protective Immunity to *Brucella abortus*," *Infection and Immunity*, 63(3):1130-1133 (1995).

Foon et al., "A Prospective Randomized Trial of $\alpha_{2B}$•1nterferon/γ-interferon or the Combination in Advanced Metastatic Renal Cell Carcinoma," *Journal of Biological Response Modifiers*, 7(6):540-545 (1988).

Frost et al., "Interleukin-6 Induction by a Muramyltripeptide Derivative in Cancer Patients," *Journal of Biological Response Modifiers*, 9(2):160-166 (1990).

Gadducci et al., "Serum Levels of Soluble Receptors for Tumor Necrosis Factor (p55 and p75 sTNFr) in Endometrial Cancer," *Anticancer Research*, 16:3125-3128 (1996).

Gatanaga et al., "Identification of TNF-LT Blocking Factor(s) in the Serum and Ultrafiltrates of Human Cancer Patients", *Lymphokine Research*, 9(2):225-229, 1990.

Gatanaga et al., "Purification and characterization of an inhibitor (soluble tumor necrosis factor receptor) for tumor necrosis factor and lymphotoxin obtained from the serum of ultrafiltrates of human cancer patients", pp. 8781-8784, 1990.

Gill et al., "Interferon-Alpha Maintenance Therapy After Cytotoxic Chemotherapy for Treatment of Acquired Immunodeficiency Syndrome-Related Kaposi's Sarcoma," *Journal of Biological Response Modifiers*, 9(5):512-516 (1990).

Greenblatt et al., "The Type B Receptor for Tumor Necrosis Factor-α Mediates DNA Fragmentation in HL-60 and U937 Cells and Differentiation in HL-60 Cells," *Blood*, 80(5):1339-1346 (1992).

Gustavson et al., "Pharmacokinetics of Teceleukin (Recombinant Human Interleukin-2) After Intravenous or Subcutaneous Administration to Patients with Cancer," *Journal of Biological Response Modifiers*, 8(4):440-449 (1989).

Handzel et al., "Immunomodulation of T Cell Deficiency in Humans by Thymic Humoral Factor: From Crude Extract to Synthetic Thymic Humoral Factor-γ2," *Journal of Biological Response Modifiers*, 9(3):269-278 (1990).

Hank et al., "Depressed In Vitro T Cell Responses Concomitant with Augmented Interleukin-2 Responses by Lymphocytes from Cancer Patients Following In Vivo Treatment with Interleukin-2," *Journal of Biological Response Modifiers*, 9(1):5-14 (1990).

Hercend et al., "Immunotherapy with Lymphokine-Activated Natural Killer Cells and Recombinant Interleukin-2: A Feasibility Trial in Metastatic Renal Cell Carcinoma," *Journal of Biological Response Modifiers*, 9(6):546-555 (1990).

Herrmann et al., "Stimulation of Granulopoiesis in Patients with Malignancy by Recombinant Human Granulocyte-Macrophage Colony-Stimulating Factor: Assessment of Two Routes of Administration," *Journal of Biological Response Modifiers*, 9(5):475-479 (1990).

Hertler et al., "A Phase I Study of T101-Ricin A Chain Immunotoxin in Refractory Chronic Lvmohocvtic Leukemia," *Journal of Biological Response Modifiers*, 7(1):97-113 (1988).

Himmler et al, "Molecular Cloning and Expressions of Human and Rat Tumor Necrosis Factor Receptor Chain (p60) and its Soluble Derivative, Tumor Necrosis Factor-Binding Protein," *DNA and Cell Biology*, 9(10):705-715 (1990).

Jablonska et al., "Release of Soluble Tumor Necrosis Factor Receptors from Polymorphonuclear Cells of Breast Cancer Patients," *Archivum Immunologiae et Therapiae Experimentalis*, 45:449-453 (1997).

Jacobs et al., "Minimal Antigenicity of Intron A in Human Recipients Demonstrated by Three Analytical Methods," *Journal of Biological Response Modifiers*, 7(5):447-456 (1988).

Jakobsen et al., "Decreased Antitoxic Activities among Children with Clinical Episodes of Malaria," *Infection and Immunity.*, 66(4):1654-1659 (1998).

Jakschies et al., "Emergence and Decay of the Human Mx Homolog in Cancer Patients During and After Interferon-α Therapy," *Journal of Biological Response Modifiers*, 9(3):305-312 (1990).

Kalmanti et al., "Serum Levels of Tumor Necrosis Factor and Soluble Interleukin 2 Receptor as Markers of Disease Activity and Prognosis in Childhood Leukemia and Lymphoma," *International Journal of Hermatoloav*, 57(2):147-152 (1993).

Kaufmann et al., "T Cells and Cytokines in Intracellular Bacterial Infections: Experiences with *Mycobacterium bovis* BCG," *Ciba Fdn. Symp.*, 195:123-136 (1995).

Kellokumpu-Lehtinen et al., "Recombinant Interferon-α2a and Vinblastine in Advanced Renal Cell Cancer: A Clinical Phase I-II Study," *Journal of Biological Response Modifiers*, 9(4):439-444 (1990).

Kessler, "Adsorptive Plasma Treatment: Optimization of Extracorporeal Devices and Systems," *Blood Purification*, 11:150-157 (1993).

Khazaeli et al., "Initial Evaluation of a Human Immunoglobulin M Monoclonal Antibody (HA-1A) in Humans," *Journal of Biological Response Modifiers*, 9(2):178-184 (1990).

Kolitz et al., "Phase I Trial of Recombinant Interleukin-2 and Cyclophosphamide: Augmentation of Cellular Immunity and T-Cell Mitogenic Response with Long-Term Administration of rIL-2," *Journal of Biological Response Modifiers*, 7(5):457-472 (1988).

Krigel et al., "Treatment of Epidemic Kaposi's Sarcoma with a Combination of Interferon-Alpha $2_b$, and Etoposide," *Journal of Biological Response Modifiers*, 7(4):359-364 (1988).

Lantz et al. "Infusion of Tumor Necrosis Factor (TNF) Causes an Increase in Circulating TNF-Binding Protein in Humans," *Cytokine*, 2(6):402-406 (1990).
Laszlo et al., "Phase I Studies of Recombinant Interferon-γ," *Journal of Biological Response Modifiers*, 9(2):185-193 (1990).
Laucella "Papel de Las Citoquinas en la Resistencia y Patologia Durante la Intecclon con *Trypanosoma cruzi," Revista Araentina de Microbiologia*, 28:99-109 (1996).
Lentz et al., "Apheresis of Low Molecular Weight Protein Fraction and the Onset of Labor," *Journal of Clinical Apheresis*, 5:62-67 (1990).
Lentz, "The Phylogeny of Oncology," *Mol. Biother.*, 2:137-144 (1990).
Lentz,"Continuous Whole Blood UltraPheresis Procedure in Patients with Metastatic Cancer", *J. Biol. Resp. Mod.*, 8:511-527, 1989.
Lentz, "The Role of Therapeutic Apheresis in the Treatment of Cancer: A Review", *Therpauetic Apheresis*, 3:40-49, 1999.
Lentz et al., Low Molecular Weight Protein Apheresis and Regression of Breast Cancer, *Japanese Journal of Apheresis*, 16:107-114, 1997.
Letterio et al., "Regulation of Immune Responses by TGF-β," *Ann Rev. Immunol.*, 16:137-161 (1998).
Litton et al., "Biological and Clinical Effects of Oral Immunomodulator 3, 6-Bis(2-piperidinoethoxy)acridine Trihydrochloride in Patients with Malignancy," *Journal of Biological Response Modifiers*, 9(1):61-70 (1990).
Lucey et al., "Type 1 and Type 2 Cytokine Dysregulation in Human Infectious, Neoplalstic, and Inflammatory Diseases," *Clinical Microbiology Reviews*, 9(4):532-562 (1996).
Maas et al., "Interleukin-2 in Cancer Treatment: Disappointing or (Still) Promising? A Review," *Cancer Immunol. Immunother*, 36:141-148 (1993).
Maca, "Inhibition of the Growth of Lewis Lung Carcinoma by Indomethacin in Conventional, Nude, and Beige Mice," *Journal of Biological Response Modifiers*, 7:568-580 (1988).
Marshall et al., "Effects of Coumarin (1, 2-Benzopyrone) and Cimetidine on Peripheral Blood Lymphocytes, Natural Killer Cells, and Monocytes in Patients with Advanced Malignancies," *Journal of Biological Response Modifiers*, 8(8):62-69 (1989).
Marshall et al, "Treatment of Renal Cell Carcinoma with Daily Low-Dose Alpha-Interferon," *Journal of Biological Respoose Modifiers*, 8(5)453-461 (1989).
Matschiner et al., "Heterogeneity of Protein C and Factor X From Human Plasma," *Current Advances in Vitamin K Research*, 135-140 (1988).
McLeod, et al. Eds, "Apheresis: Principles and Practice", AABB Press, Bethesda, MD, 1997.
Miles et al., "Induction of Soluble Tumour Necrosis Factor Receptors During Treatment with Interleukin-2," *Brit. J. Cancer*, 66:1195-1199 (1992).
Mittelman et al., "Treatment of Patients with Advanced Cancer Using Multiple Long-Term Cultrued Lymphokine-Activated Killer (LAK) Cell Infusions and Recombinant Human Interleukin-2", *Journal of Biological Response Modifiers*, 1989, 8:468-478.
Mitteregger et al., "In Vitro Cell Culture Systems as the Basis for an Extracorporeal Blood Purification Strategy in Multiorgan Failure Treatment," *Therapeutic Apheresis*, 3(3):257-263 (1999).
Musiani et al., "Effect of Low Doses of Interleukin-2 Injected Perilymphatically and Peritumorally in Patients with Advanced Primary Head and Neck Squamous Cell Carcinoma," *Journal of Biological Response Modifiers*, 8(6):571-578 (1989).
Neidhart et al., "Phase I Study of Recombinant Methionyl Human Consensus Interferon (r-metHuIFNCon$_1$)," *Journal of Biological Response Modifiers*, 7(3):240-248 (1988).
Oratz et al., "Antimelanoma Monoclonal Antibody-Ricin A Chain Immunoconjugate (XMMME-001-RRA) Plus Cyclophosphamide in the Treatment of Metastatic Malignant Melanoma: Results of a Phase II Trial," *Journal of Biological Response Modifiers*, 9(4):345-354 (1990).
Oratz et al., "Induction of Tumor-Infiltrating Lymphocytes in Human Malignant Melanoma Metastases by Immunization to Melanoma Antigen Vaccine," *Journal of Biological Response Modifiers*, 8(4):355-358 (1989).
Pais et al., "Pharmacokinetics of Recombinant Interleukin-2 in Children with Malignancies: A Pediatric Oncology Group Study," *Journal of Biological Response Modifiers*, 9(5):517-521 (1990).
Panka et al., "Variable region framework differences result in decreased or increased affinity of variant anti-digoxin antibodies," *Proc Natl. Acad. Sci. USA* 85:3080-3084 (1988).
Paolozzi et al., "Phase I Trial of Recombinant Interleukin-2 and Recombinant β-Interferon in Refractory Neoplastic Diseases," *Journal of Biological Response Modifiers*, 8(2):122-139 (1989).
Perez et al., "A Phase I Trial of Recombinant Human Gamma Interferon (IFN-$\gamma_{4A}$) in Patients with Advanced Malignancy," *Journal of Biological Response Modifiers*, 7(3):309-317 (1988).
Quesada et al., "Recombinant Interferon Alpha and Gamma in Combination as Treatment for Metastatic Renal Cell Carcinoma," *Journal of Biological Response Modifiers*, 7(3):234-239 (1988).
Rabinowitz et al., "Hemolytic Anemia in a Cancer Patient Treated with Recombinant Interferon-γ," *Journal of Biological Response Modifiers*, 9(2):256-259 (1990).
Reimann et al., Suppression of the Immune Response by Micro-Organisms, *Scand. J. Immunol.*, 31:543-546 (1990).
Riffkin et al., Defence Against the Immune Barrage: Helminth Survival Strategies, *Immunology and Cell Biology*, 74:564-574 (1996).
Romani et al., "T Helper Cell Dichotomy to *Candida albicans*: Implications for Pathology, Therapy, and Vaccine Design," *Immunol. Res.*, 14:148-162 (1995).
Rosenthal et al., "The In Vitro Function of Lymphocytes from 25 Cancer Patients Receiving Four to Seven Consecutive Days of Recombinant IL-2," *Journal of Biological Response Modifiers*, 7(2):123-139 (1988).
Rudikoff et al., "Single amino acid substitution altering antigen-binding specificity," *Proc. Natl. Acad. Sci.* USA, 79:1979-1983 (1982).
Rybak et al., "Interferon Therapy of Relapsed and Refractory Hodgkin's Disease: Cancer and Leukemia Group B Study 8652," *Journal of Biological Response Modifiers*, 9(1):1-4 (1990).
Sarna et al., "A Pilot Study of Intralymphatic Interleukin-2. II. Clinical and Biological Effects," *Journal of Biological Response Modifiers*, 9(1):81-86 (1990).
Sarna et al., "Systemic Administration of Recombinant Methionyl Human Interleukin-2 (Ala 125) to Cancer Patients: Clinical Results," *Journal of Biological Response Modifiers*, 8(1): 16-24 (1989).
Sarthou et al., "Prognostic Value of *Anti-Plasmodium falciparum*—Specific Immunoglobulin G3, Cytokines, and Their Soluble Receptors in West African Patients with Severe Malaria," *Infection and Immunity*, 65(8):3271-3276 (1997).
Sato et al., "Induction of Bone Formation in an Adenoid Cystic Carcinoma of the Maxillary Sinus by Adoptive Immunotherapy Involving Intra-Arterial Injection of Lymphokine-Activated Killer Cells and Recombinant Interleukin-2 in Combination with Radiotherapy," *Journal of Biological Response Modifiers*, 9(3):329-334(1990).
Schaadt et al., "Phase II Study of Recombinant Human Tumor Necrosis Factor in Colorectal Carcinoma," *Journal of Biological Response Modifiers*, 9(2):247-250 (1990).
Schall et al., "Molecular Cloning and Expressions of a Receptor for Human Tumor Necrosis Factor," *Cell*, 61:361-370 (1990).
Scheithauer et al., "Combined α-2C-Interferon/VMCP Polychemotherapy Versus VMCP Polychemotherapy as Induction Therapy in Multiple Myeloma: A Prospective Randomized Trial," *Journal of Biological Response Modifiers*, 8(2):109-115 (1989).
Schiller et al., "A Phase I Trial of Interferon-α-2a plus Cyclophosphamide, Vincristine, Prednisone, and Doxorubicin," *Journal of Biological Response Modifiers*, 8(3):252-261 (1989).
Seckinger et al., "Purification and Biologic Characterization of a Specific Tumor Necrosis Factor α Inhibitor," *Journal of Biological Chemistry*, 264(20):11966-11973 (1989).
Seigler et al., "Melanoma Patient Antibody Responses to Melanoma Tumor-Associated Antigens Defined by Murine Monoclonal Antibodies," *Journal of Biological Response Modifiers*, 8(1):37-52 (1989).
Selinsky et al., "Multifaceted Inhibition of Anti-Tumour Immune Mechanisms by Soluble Tumour Necrosis Factor Receptor Type I," *Immunology*, 94:88-93 (1998).

Selinsky et al., "Soluble Tumor Necrosis Factor Receptor Type I Enhances Tumor Development and Persistence In Vivo," *Cellular Immunology*, 200:81-87 (2000).
Shau et al., "A Pilot Study of Intralymphatic Interleukin-2. I. Cytotoxic and Surface Marker Changes of Peripheral Blood Lymohocytes," *Journal of Biological Response Modifiers*, 9(1):71-80 (1990).
Sidhu et al., "Tumor Necrosis Factor Activities and Cancer Therapy—A Perspective," *Pharmacol. Ther.*, 57:79-128 (1993).
Sieling et al., "Immunosuppressive Roles for IL-10 and IL-4 in Human Infection," *J. Immunol.*, 150:5501-5510 (1993).
Spriggs, "One Step Ahead of the Game: Viral Immunomodulatory Molecules," *Annu. Rev. Immunol.*, 14:101-130 (1996).
Steger et al., "Long-Term Remission in a Patient with Erythroleukemia Following Interferon-α Treatment," *Journal of Biological Response Modifiers*, 8(4):351-354 (1989).
Steinmetz et al., "Phase I Study of 24-Hour Continuous Intravenous Infusion of Recombinant Human Tumor Necrosis Factor," *Journal of Biological Response Modifiers*, 7(5):417-423 (1988).
Sznol et al., "A Phase I Study of High-Dose Interleukin-2 in Combination with Interferon-$\alpha_{2b}$," *Journal of Biological Response Modifiers*, 9(6):529-537 (1990).
Tavernier et al., "Analysis of the Structure-Function Relationship of Tumour Necrosis Factor Human/Mouse Chimeric TNF Proteins: General Properties and Epitope Analysis," *J. Mol. Biol.*, 211:493-501 (1990).
Trigg et al., "α-Interferon Therapy for Lymphoproliferative Disorders Developing in Two Children Following Bone Marrow Transolants," *Journal of Biological Response Modifiers*, 8(6):603-613 (1989).
Trinchieri et al., "Cytokine Cross-Talk Between Phagocytic Cells and Lymphocytes: Relevance for Differentiation/Activation of Phagocytic Cells and Regulation of Adaptive Immunity," *Journal of Cellular Biochemistry*, 53:301-308 (1993).
Trump et al., "Interferon-α-n1 and Continuous Infusion Vinblastine for Treatment of Advanced Renal Cell Carcinoma," *Journal of Biological Response Modifiers*, 9(1):108-111 (1990).
Umiel et al., "Recombinant Interleukin-2-Activated Intracavitary Lymphocytes: Phenotypic Characteristics and Effector Function," *Journal of Biological Response Modifiers*, 8(4):409-421 (1989).
Van Ostade et al., "Structure-Activity Studies of Human Tumour Necrosis Factors," *Protein Engineering*, 7(1):5-22 (1994).
Van Ostade et al., "Localization of the Active Site of Human Tumour Necrosis Factor (hTNF) by Mutational Analysis," *EMBO Journal*, 10(4):827-836 (1991).
Von Hoff et al., "Phase II Evaluation of Recombinant γ-Interferon in Patients with Advanced Pancreatic Carcinoma: A Southwest Oncology Group Study," *Journal of Biological Response Modifiers*, 9(6):584-587 (1990).
Walsh et al., "Phase I Study of the Combination of Alpha-2 Interferon and Cisplatinum," *Journal of Biological Response Modifiers*, 8(1):11-15 (1989).
Weil-Hillman et al., "Transient Decrease in IL-2-Responsive Lymphocytes 24 Hours After Initiation of Continuous IL-2 Infusion in Cancer Patients," *Journal of Biological Response Modifiers*, 7(5):424-437 (1988).
Whitehead et al., "A Phase II Trial of Recombinant Tumor Necrosis Factor in Patients with Metastatic Colorectal Adenocarcinoma: A Southwest Oncology Group Study," *Journal of Biological Response Modifiers*, 9(6):588-591 (1990).
Yamagashi et al., "Mutational Analysis fo Structure-Activity Relationships in Human Tumor Necrosis Factor-Alpha," *Protein Engineering*, 3(8):713-719 (1990).
Yelavarthi et al., "Analysis of p60 and p80 tumor necrosis factor-c Receptor Messenger RNA and Protein in Human Placentas," *American Journal of Pathology*, 143(4):1131-1141 (1993).
Zamkoff et al., "A Phase I Trial of Subcutaneously Administered Recombinant Tumor Necrosis Factor to Patients with Advanced Malignancy," *Journal of Biological Response Modifiers*, 8(5):539-552 (1989).
"Anti-human sTNF RI (TNF-BPI) Antibody," *R&D Systems*, Catalog No. AB-225-PB, Lot No. DB104061.
2013 "Anti-mouse sTNF R1/TNFRSF1A Antibody," *R&D Systems*, Catalog No. AF-425-PB, Lot No. ADF01.
"Mouse (monoclonal) Anti-Human Soluble Tumor Necrosis Factor Receptor I (sTNF-RI) Capture Antibody, Product Analysis Sheet," *Biosource*, Catalog No. AHR3912, Lot No. 3B8/1 (Clone No. 943BC51G1).
"Human TCR V beta 6.7 MAb (clone OT145)," *Pierce Biotechnology*.
Application and File History for U.S. Appl. No. 11/234,057, filed Sep. 22, 2005. Inventor: Mark Douglas Howell.
Application and File History for U.S. Appl. No. 10/071,829, filed Feb. 7, 2002. Inventor: Mark D. Howell, Cheryl L. Selinsky, Leland C. Leber.
Application and File History for U.S. Appl. No. 09/444,144, filed Nov. 20, 1999. Inventor: Mark D. Howell, Cheryl L. Selinsky, Leland C. Leber.

* cited by examiner

```
                10        20        30        40        50        60        70        80
                 |         |         |         |         |         |         |         |
.RSSS...S.KPVAHVVAN.....QL.W....ANAL.ANG..L.DNQL VP..GLYLIYSQVLF.G.GCP.....LTHT.  CONS
LRSSSQNSSDKPVAHVVANHQVEEQLEWLSQRANALLANGMDLKDNQLVVPADGLYLVYSQVLFKGQGCP-DVVLLTHTV  MUS
LRSSSQNSSDKPVAHVVANHQAEEQLEWLSQRANALLANGMDLKDNQLVVPADGLYLIYSQVLFKGQGCP-DYVLLTHTV  RAT
LRSASRALSDKPLAHVVANPQVEGQLQWLSQRANALLANGMKLTDNQLVVPADGLYLIYSQVLFSGQGCR-SYVLLTHTV  RAB
LRSSSRTPSDKPVAHVVANPEAEGQLQRLSRRANALLANGVELTDNQLKVPSDGLYLIYSQVLFTGQGCPSTHVLLTHAI  CAT
VLSSSRTPSDKPVAHVVANPEAEGQLQWLSRRANALLANGVELTDNQLIVPSDGLYLIYSQVLFKGQGCPSTHVLLTHTI  DOG
LRSSSQASNNKPVAHVVANLSAPGQLRWGDSYANALMANGVELKDNQLVVPTDGLYLIYSQVLFRGHGCPSTPLFLTHTI  SHEP
LRSSSQASSNKPVAHVVANISAPGQLRWGDSYANALKANGVELKDNQLVVPTDGLYLIYSQVLFRGHGCPSTPLFLTHTI  GOAT
LRSSSRTPSDKPVAHVVANPQAEGQLQWLSGRANALLANGVKLTDNQLVVPLDGLYLIYSQVLFKGQGCPSTHVLLTHTI  HORSE
LRSSSQASSNKPVAHVVADINSPGQLRWWDSYANALMANGVQLEDNQLVVPAEGLYLIYSQVLFRGQGCP-PPPVLTHTI  COW
LRSSSQT-SDKPVAHVVANVKAEGQLQWQSGYANALLANGVKLKDNQLVVPTDGLYLIYSQVLFRGQGCPSTNVFLTHTI  PIG
VRSSSRTPSDKPVAHVVANPQAEGQLQWLNRRANALLANGVELRDNQLVVPSEGLYLIYSQVLFKGQGCPSTHVLLTHTI  HUM

               90       100       110       120       130       140       150
                |         |         |         |         |         |         |
SR.A.SY..KVN.LSAIKSPC...TPE.AE.KPWYEPIY.GGVFQLEK.D.LS.E.N.P.YLD.AESGQVYFG.IAL  CONS
SRFAISYQEKVNLLSAVKSPCPKDTPEGAELKPWYEPIYLGGVFQLEKGDQLSAEVNLPKYLDFAESGQVYFGVIAL  MUS
SRFAISYQEKVSLLSAIKSPCPKDTPEGAELKPWYEPMYLGGVFQLEKGDLLSAEVNLPKYLDITESGQVYFGVIAL  RAT
SRFAVSYPNKVNLLSAIKSPCHRETPEEAEPMAWYEPIYLGGVFQLEKGDRLSTEVNQPEYLDLAESGQVYFGIIAL  RAB
SRFAVSYQTKVNLLSAIKSPCQRETPEGAEAKPWYEPIYLGGVFQLEKGDRLSTEINLPAYLDFAESGQVYFGIIAL  CAT
SRFAVSYQTKVNLLSAIKSPCQRETPEGTEAKPWYEPIYLGGVFQLEKGDRLSAEINLPNYLDFAESGQVYFGIIAL  DOG
SRIAVSYQTKVNILSAIKSPCHRETLEGAEAKPWYEPIYQGGVFQLEKGDRLSAEINLPEYLDYAESGQVYFGIIAL  SHEEP
SRIAVSYQTKVNILSAIKSPCHRETPE-AEAKPWYEPIYQGGVEQLEKGDRLSAEINQPEYLDYAESGQVYFGIIAL  GOAT
SRLAVSYPSKVNLLSAIKSPCHTESPEQAEAKPWYEPIYLGGVFQLEKGDQLSAEINQPNYLDFAESGQVYFGIIAL  HORSE
SRIAVSYQTKVNILSAIKSPCHRETPEWAEAKPWYEPIYQGGVFQLEKDDRLSAEINLPDYLDYAESGQVYFGIIAL  COW
SRIAVSYQTKVNLLSAIKSPCQRETPEGAEAKPWYEPIYLGGVFQLEKDDRLSAEINLPDYLDFAESGQVYFGIIAL  PIG
SRIAVSYQTKVNLLSAIKSPCQRETPEGAEAKPWYEPIYLGGVFQLEKGDRLSAEINRPDYLDFAESGQVYFGIIAL  HUM
```

*FIG. 3A*

```
          10        20        30        40
           |         |         |         |
.RSSS...S.KPVAHVVAN.....QL.W....ANAL.ANG CONSERVED
VRSSSRTPSDKPVAHVVANPQAEGQLQWLNRRANALLANG HUMAN
VRSSSRTPSDKPVAHVVANPQAEGQLQWLNPRANALLANG MUTEIN 1
VRSSSRTPSDKPVAHVVANPQAEGQLQWLNRRAYALLANG MUTEIN 2
VRSSSRTPSDKPVAHVVANPQAEGQLQWLNRRANALLANG MUTEIN 3
VRSSSRTPSDKPVAHVVANPQAEGQLQWLNRRANALLANG MUTEIN 4
VRSSSRTPSDKPVAHVVANPQAEGQLQWLNRRANALLANG MUTEIN 5
VRSSSRTPSDKPVAHVVANPQAEGQLQWLNRRANALLANG MUTEIN 6

          50        60        70        80
           |         |         |
..L.DNQL VP..GLYLIYSQVLF.G.GCP.....LTHT. C
VELRDNQLVVPSEGLYLIYSQVLFKGQGCPSTHVLLTHTI H
VELRDNQLVVPSEGLYLIYSQVLFKGQGCPSTHVLLTHTI M1
VELRDNQLVVPSEGLYLIYSQVLFKGQGCPSTHVLLTHTI M2
VELRDNQLVVPSEGLYLIYSQVLFKGQGCPSTHVLLTHTI M3
VELRDNQLVVPSEGLYLIYSQVLFKGQGCPSTHVLLTHTI M4
VELRDNQLVVPSEGLYLIYSQVLFKGQGCPSTHVLLTHTI M5
VELRDNQLVVPSEGLYLIYSQVLFKGQGCPSTHVLLTHTI M6

          90        100       110       120
           |         |         |         |
SR.A.SY..KVN.LSAIKSPC...TPE.AE.KPWYEPIY. C
SRIAVSYQTKVNLLSAIKSPCQRETPEGAEAKPWYEPIYL H
SRIAVSYQTKVNLLSAIKSPCQRETPEGAEAKPWYEPIYL M1
SRIAVSYQTKVNLLSAIKSPCQRETPEGAEAKPWYEPIYL M2
SRIAVSYQTKVNLLSAIKSPCQRETPEGAEAKPWYELIYL M3
SRIAVSYQTKVNLLSAIKSPCQRETPEGAEAKPWYEPIYL M4
SRIAVSYQTKVNLLYAIKSPCQRETPEGAEAKPWYEPIYL M5
SRIAVSYQTKVNLLSAIKSPCQRETPEGAEAKPWFEPIYL M6

          130       140       150
           |         |         |
GGVFQLEK.D.LS.E.N.P.YLD.AESGQVYFG.IAL C
GGVFQLEKGDRLSAEINRPDYLDFAESGQVYFGIIAL H
GGVFQLEKGDRLSAEINRPDYLDFAESGQVYFGIIAL M1
GGVFQLEKGDRLSAEINRPDYLDFAESGQVYFGIIAL M2
GGVFQLEKGDRLSAEINRPDYLDFAESGQVYFGIIAL M3
GGVFQLEKGDRLSAEINRPDYLDFAEYGQVYFGIIAL M4
GGVFQLEKGDRLSAEINRPDYLDFAESGQVYFGIIAL M5
GGVFQLEKGDRLSAEINRPDYLDFAESGQVYFGIIAL M6
```

*FIG. 3B*

```
          10                  20           30                40
          |                   |            |                 |
```
$X_1RSSSX_2SX_3KPVAHVVANX_4QLX_5WX_6ANALX_7ANG$

```
               50                  60                     70           80
               |                   |                      |            |
```
$X_8LX_9DNQLX_{10}VPX_{11}GLYLIYSQVLFX_{12}GX_{13}GCPX_{14}LTHTX_{15}$

```
                   90                   100                   110                   120
                   |                    |                     |                     |
```
$SRX_{16}AX_{17}SYX_{18}KVNX_{19}LSAIKSPCX_{20}TPEX_{21}AEX_{22}KPWYEPIYX_{23}$

```
              130                            140                       150
              |                              |                         |
```
$GGVFQLEKX_{24}DX_{25}LSX_{26}EX_{27}NX_{28}PX_{29}YLDX_{30}AESGQVYFGX_{31}IAL$

*FIGURE 3C*

```
                         SEQUENCE LISTING

<160> NUMBER OF SEQ ID NOS: 46

<210> SEQ ID NO 1
<211> LENGTH: 108
<212> TYPE: PRT
<213> ORGANISM: Artificial Sequence
<220> FEATURE:
<223> OTHER INFORMATION: Chemically synthesized TNFalpha conserved amino
      acids across species

<400> SEQUENCE: 1

Arg Ser Ser Ser Ser Lys Pro Val Ala His Val Val Ala Asn Gln Leu
 1               5                  10                  15

Trp Ala Asn Ala Leu Ala Asn Gly Leu Asp Asn Gln Leu Val Pro Gly
            20                  25                  30

Leu Tyr Leu Ile Tyr Ser Gln Val Leu Phe Gly Gly Cys Pro Leu Thr
        35                  40                  45

His Thr Ser Arg Ala Ser Tyr Lys Val Asn Leu Ser Ala Ile Lys Ser
    50                  55                  60

Pro Cys Thr Pro Glu Ala Glu Lys Pro Trp Tyr Glu Pro Ile Tyr Gly
65                  70                  75                  80

Gly Val Phe Gln Leu Glu Lys Asp Leu Ser Glu Asn Pro Tyr Leu Asp
                85                  90                  95

Ala Glu Ser Gly Gln Val Tyr Phe Gly Ile Ala Leu
            100                 105


<210> SEQ ID NO 2
<211> LENGTH: 157
<212> TYPE: PRT
<213> ORGANISM: Homo sapiens
```

<400> SEQUENCE: 2

```
Val Arg Ser Ser Ser Arg Thr Pro Ser Asp Lys Pro Val Ala His Val
 1               5                  10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155
```

<210> SEQ ID NO 3
<211> LENGTH: 157
<212> TYPE: PRT
<213> ORGANISM: Artificial Sequence
<220> FEATURE:
<223> OTHER INFORMATION: Chemically synthesized TNFalpha mutein

<400> SEQUENCE: 3

```
Val Arg Ser Ser Ser Arg Thr Pro Ser Asp Lys Pro Val Ala His Val
 1               5                  10                  15

Val Ala Asn Pro Gln Ala Glu Gly Gln Leu Gln Trp Leu Asn Pro Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155
```

<210> SEQ ID NO 4
<211> LENGTH: 157
<212> TYPE: PRT
<213> ORGANISM: Artificial Sequence
<220> FEATURE:
<223> OTHER INFORMATION: Chemically synthesized TNFalpha mutein

<400> SEQUENCE: 4

Val Arg Ser Ser Ser Arg Thr Pro Ser Asp Lys Pro Val Ala His Val
 1               5                  10                  15

Val Ala Asn Pro Gln Ala Glu Gly Gln Leu Gln Trp Leu Asn Arg Arg
            20                  25                  30

Ala Tyr Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155

<210> SEQ ID NO 5
<211> LENGTH: 157
<212> TYPE: PRT
<213> ORGANISM: Artificial Sequence
<220> FEATURE:
<223> OTHER INFORMATION: Chemically synthesized TNFalpha mutein

<400> SEQUENCE: 5

Val Arg Ser Ser Ser Arg Thr Pro Ser Asp Lys Pro Val Ala His Val
 1               5                  10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Leu Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155

<210> SEQ ID NO 6
<211> LENGTH: 157
<212> TYPE: PRT
<213> ORGANISM: Artificial Sequence
<220> FEATURE:
<223> OTHER INFORMATION: Chemically synthesized TNFalpha mutein -continued

<400> SEQUENCE: 6

Val Arg Ser Ser Ser Arg Thr Pro Ser Asp Lys Pro Val Ala His Val
1 5 10 15

Val Ala Asn Pro Gln Ala Glu Gly Gln Leu Gln Trp Leu Asn Arg Arg
20 25 30

Ala Asn Ala Leu Leu Ala Asn Gly Val Glu Leu Arg Asp Asn Gln Leu
35 40 45

Val Val Pro Ser Glu Gly Leu Tyr Leu Ile Tyr Ser Gln Val Leu Phe
50 55 60

Lys Gly Gln Gly Cys Pro Ser Thr His Val Leu Leu Thr His Thr Ile
65 70 75 80

Ser Arg Ile Ala Val Ser Tyr Gln Thr Lys Val Asn Leu Leu Ser Ala
85 90 95

Ile Lys Ser Pro Cys Gln Arg Glu Thr Pro Glu Gly Ala Glu Ala Lys
100 105 110

Pro Trp Tyr Glu Pro Ile Tyr Leu Gly Gly Val Phe Gln Leu Glu Lys
115 120 125

Gly Asp Arg Leu Ser Ala Glu Ile Asn Arg Pro Asp Tyr Leu Asp Phe
130 135 140

Ala Glu Tyr Gly Gln Val Tyr Phe Gly Ile Ile Ala Leu
145 150 155

<210> SEQ ID NO 7
<211> LENGTH: 157
<212> TYPE: PRT
<213> ORGANISM: Artificial Sequence
<220> FEATURE:
<223> OTHER INFORMATION: Chemically synthesized TNFalpha mutein

<400> SEQUENCE: 7

Val Arg Ser Ser Ser Arg Thr Pro Ser Asp Lys Pro Val Ala His Val
1 5 10 15

Val Ala Asn Pro Gln Ala Glu Gly Gln Leu Gln Trp Leu Asn Arg Arg
20 25 30

Ala Asn Ala Leu Leu Ala Asn Gly Val Glu Leu Arg Asp Asn Gln Leu
35 40 45

Val Val Pro Ser Glu Gly Leu Tyr Leu Ile Tyr Ser Gln Val Leu Phe
50 55 60

Lys Gly Gln Gly Cys Pro Ser Thr His Val Leu Leu Thr His Thr Ile
65 70 75 80

Ser Arg Ile Ala Val Ser Tyr Gln Thr Lys Val Asn Leu Leu Tyr Ala
85 90 95

Ile Lys Ser Pro Cys Gln Arg Glu Thr Pro Glu Gly Ala Glu Ala Lys
100 105 110

Pro Trp Tyr Glu Pro Ile Tyr Leu Gly Gly Val Phe Gln Leu Glu Lys
115 120 125

Gly Asp Arg Leu Ser Ala Glu Ile Asn Arg Pro Asp Tyr Leu Asp Phe
130 135 140

Ala Glu Ser Gly Gln Val Tyr Phe Gly Ile Ile Ala Leu
145 150 155

<210> SEQ ID NO 8
<211> LENGTH: 157
<212> TYPE: PRT
<213> ORGANISM: Artificial Sequence
<220> FEATURE:
<223> OTHER INFORMATION: Chemically synthesized TNFalpha mutein -continued

<400> SEQUENCE: 8

Val Arg Ser Ser Ser Arg Thr Pro Ser Asp Lys Pro Val Ala His Val
1 5 10 15

Val Ala Asn Pro Gln Ala Glu Gly Gln Leu Gln Trp Leu Asn Arg Arg
20 25 30

Ala Asn Ala Leu Leu Ala Asn Gly Val Glu Leu Arg Asp Asn Gln Leu
35 40 45

Val Val Pro Ser Glu Gly Leu Tyr Leu Ile Tyr Ser Gln Val Leu Phe
50 55 60

Lys Gly Gln Gly Cys Pro Ser Thr His Val Leu Leu Thr His Thr Ile
65 70 75 80

Ser Arg Ile Ala Val Ser Tyr Gln Thr Lys Val Asn Leu Leu Ser Ala
85 90 95

Ile Lys Ser Pro Cys Gln Arg Glu Thr Pro Glu Gly Ala Glu Ala Lys
100 105 110

Pro Trp Phe Glu Pro Ile Tyr Leu Gly Gly Val Phe Gln Leu Glu Lys
115 120 125

Gly Asp Arg Leu Ser Ala Glu Ile Asn Arg Pro Asp Tyr Leu Asp Phe
130 135 140

Ala Glu Ser Gly Gln Val Tyr Phe Gly Ile Ile Ala Leu
145 150 155

<210> SEQ ID NO 9
<211> LENGTH: 157
<212> TYPE: PRT
<213> ORGANISM: Artificial Sequence
<220> FEATURE:
<223> OTHER INFORMATION: Representative consensus TNFalpha mutein sequence that would be chemically synthesized
<220> FEATURE:
<221> NAME/KEY: VARIANT
<222> LOCATION: 1
<223> OTHER INFORMATION: Xaa=Leu or Val
<220> FEATURE:
<221> NAME/KEY: VARIANT
<222> LOCATION: 6
<223> OTHER INFORMATION: Xaa=Gln or Arg
<220> FEATURE:
<221> NAME/KEY: VARIANT
<222> LOCATION: 7
<223> OTHER INFORMATION: Xaa=Asn, Ala or Thr
<220> FEATURE:
<221> NAME/KEY: VARIANT
<222> LOCATION: 8
<223> OTHER INFORMATION: Xaa=Ser, Leu or Pro and may or may not be present
<220> FEATURE:
<221> NAME/KEY: VARIANT
<222> LOCATION: 10
<223> OTHER INFORMATION: Xaa=Asp or Asn
<220> FEATURE:
<221> NAME/KEY: VARIANT
<222> LOCATION: (20)...(20)
<223> OTHER INFORMATION: Xaa=His, Pro, Leu Ile or Val
<220> FEATURE:
<221> NAME/KEY: VARIANT
<222> LOCATION: (21)...(21)
<223> OTHER INFORMATION: Xaa=Gln,Glu,Ser, Asn or Lys
<220> FEATURE:
<221> NAME/KEY: VARIANT
<222> LOCATION: (22)...(22)
<223> OTHER INFORMATION: Xaa=Val, Ala or Ser
<220> FEATURE:
<221> NAME/KEY: VARIANT
<222> LOCATION: (23)...(23)
<223> OTHER INFORMATION: Xaa=Glu or Pro
<220> FEATURE:
<221> NAME/KEY: VARIANT
<222> LOCATION: (24)...(24)

<223> OTHER INFORMATION: Xaa=Glu or Gly
<220> FEATURE:
<221> NAME/KEY: VARIANT
<222> LOCATION: (27)...(27)
<223> OTHER INFORMATION: Xaa=Glu, Gln or Arg
<220> FEATURE:
<221> NAME/KEY: VARIANT
<222> LOCATION: (29)...(29)
<223> OTHER INFORMATION: Xaa=Leu, Gly,Trp or Gln
<220> FEATURE:
<221> NAME/KEY: VARIANT
<222> LOCATION: (30)...(30)
<223> OTHER INFORMATION: Xaa=Ser, Asp, or Asn
<220> FEATURE:
<221> NAME/KEY: VARIANT
<222> LOCATION: (31)...(31)
<223> OTHER INFORMATION: Xaa=Gln, Arg, Ser or Gly
<220> FEATURE:
<221> NAME/KEY: VARIANT
<222> LOCATION: (32)...(32)
<223> OTHER INFORMATION: Xaa=Arg or Tyr
<220> FEATURE:
<221> NAME/KEY: VARIANT
<222> LOCATION: (37)...(37)
<223> OTHER INFORMATION: Xaa=Leu, Met or Lys
<220> FEATURE:
<221> NAME/KEY: VARIANT
<222> LOCATION: (41)...(41)
<223> OTHER INFORMATION: Xaa=Met or Val

<400> SEQUENCE: 9

```
Xaa Arg Ser Ser Ser Xaa Xaa Xaa Ser Xaa Lys Pro Val Ala His Val
 1               5                  10                  15

Val Ala Asn Xaa Xaa Xaa Xaa Xaa Gln Leu Xaa Trp Xaa Xaa Xaa Xaa
            20                  25                  30

Ala Asn Ala Leu Xaa Ala Asn Gly Xaa Xaa Leu Xaa Asp Asn Gln Leu
        35                  40                  45

Xaa Val Pro Xaa Xaa Gly Leu Tyr Leu Ile Tyr Ser Gln Val Leu Phe
    50                  55                  60

Xaa Gly Xaa Gly Cys Pro Xaa Xaa Xaa Xaa Xaa Leu Thr His Thr Xaa
65                  70                  75                  80

Ser Arg Xaa Ala Xaa Ser Tyr Xaa Xaa Lys Val Asn Xaa Leu Ser Ala
                85                  90                  95

Ile Lys Ser Pro Cys Xaa Xaa Xaa Thr Pro Glu Xaa Ala Glu Xaa Lys
            100                 105                 110

Pro Trp Tyr Glu Pro Ile Tyr Xaa Gly Gly Val Phe Gln Leu Glu Lys
        115                 120                 125

Xaa Asp Xaa Leu Ser Xaa Glu Xaa Asn Xaa Pro Xaa Tyr Leu Asp Xaa
    130                 135                 140

Ala Glu Ser Gly Gln Val Tyr Phe Gly Xaa Ile Ala Leu
145                 150                 155
```

<210> SEQ ID NO 10
<211> LENGTH: 156
<212> TYPE: PRT
<213> ORGANISM: Mus musculus

<400> SEQUENCE: 10

```
Leu Arg Ser Ser Ser Gln Asn Ser Ser Asp Lys Pro Val Ala His Val
 1               5                  10                  15

Val Ala Asn His Gln Val Glu Glu Gln Leu Glu Trp Leu Ser Gln Arg
            20                  25                  30

Ala Asn Ala Leu Leu Ala Asn Gly Met Asp Leu Lys Asp Asn Gln Leu
        35                  40                  45

Val Val Pro Ala Asp Gly Leu Tyr Leu Val Tyr Ser Gln Val Leu Phe
```

```
    50                  55                  60

Lys Gly Gln Gly Cys Pro Asp Val Val Leu Leu Thr His Thr Val Ser
65                  70                  75                  80

Arg Phe Ala Ile Ser Tyr Gln Glu Lys Val Asn Leu Leu Ser Ala Val
                85                  90                  95

Lys Ser Pro Cys Pro Lys Asp Thr Pro Glu Gly Ala Glu Leu Lys Pro
            100                 105                 110

Trp Tyr Glu Pro Ile Tyr Leu Gly Gly Val Phe Gln Leu Glu Lys Gly
        115                 120                 125

Asp Gln Leu Ser Ala Glu Val Asn Leu Pro Lys Tyr Leu Asp Phe Ala
    130                 135                 140

Glu Ser Gly Gln Val Tyr Phe Gly Val Ile Ala Leu
145                 150                 155


<210> SEQ ID NO 11
<211> LENGTH: 156
<212> TYPE: PRT
<213> ORGANISM: Rattus sp.

<400> SEQUENCE: 11

Leu Arg Ser Ser Ser Gln Asn Ser Ser Asp Lys Pro Val Ala His Val
 1               5                  10                  15

Val Ala Asn His Gln Ala Glu Glu Gln Leu Glu Trp Leu Ser Gln Arg
            20                  25                  30

Ala Asn Ala Leu Leu Ala Asn Gly Met Asp Leu Lys Asp Asn Gln Leu
        35                  40                  45

Val Val Pro Ala Asp Gly Leu Tyr Leu Ile Tyr Ser Gln Val Leu Phe
    50                  55                  60

Lys Gly Gln Gly Cys Pro Asp Tyr Val Leu Leu Thr His Thr Val Ser
65                  70                  75                  80

Arg Phe Ala Ile Ser Tyr Gln Glu Lys Val Ser Leu Leu Ser Ala Ile
                85                  90                  95

Lys Ser Pro Cys Pro Lys Asp Thr Pro Glu Gly Ala Glu Leu Lys Pro
            100                 105                 110

Trp Tyr Glu Pro Met Tyr Leu Gly Gly Val Phe Gln Leu Glu Lys Gly
        115                 120                 125

Asp Leu Leu Ser Ala Glu Val Asn Leu Pro Lys Tyr Leu Asp Ile Thr
    130                 135                 140

Glu Ser Gly Gln Val Tyr Phe Gly Val Ile Ala Leu
145                 150                 155


<210> SEQ ID NO 12
<211> LENGTH: 156
<212> TYPE: PRT
<213> ORGANISM: Oryctolagus cuniculus

<400> SEQUENCE: 12

Leu Arg Ser Ala Ser Arg Ala Leu Ser Asp Lys Pro Leu Ala His Val
 1               5                  10                  15

Val Ala Asn Pro Gln Val Glu Gly Gln Leu Gln Trp Leu Ser Gln Arg
            20                  25                  30

Ala Asn Ala Leu Leu Ala Asn Gly Met Lys Leu Thr Asp Asn Gln Leu
        35                  40                  45

Val Val Pro Ala Asp Gly Leu Tyr Leu Ile Tyr Ser Gln Val Leu Phe
    50                  55                  60

Ser Gly Gln Gly Cys Arg Ser Tyr Val Leu Leu Thr His Thr Val Ser
65                  70                  75                  80
```

```
Arg Phe Ala Val Ser Tyr Pro Asn Lys Val Asn Leu Leu Ser Ala Ile
                85                  90                  95

Lys Ser Pro Cys His Arg Glu Thr Pro Glu Glu Ala Glu Pro Met Ala
            100                 105                 110

Trp Tyr Glu Pro Ile Tyr Leu Gly Gly Val Phe Gln Leu Glu Lys Gly
        115                 120                 125

Asp Arg Leu Ser Thr Glu Val Asn Gln Pro Glu Tyr Leu Asp Leu Ala
    130                 135                 140

Glu Ser Gly Gln Val Tyr Phe Gly Ile Ile Ala Leu
145                 150                 155


<210> SEQ ID NO 13
<211> LENGTH: 157
<212> TYPE: PRT
<213> ORGANISM: Felis catus

<400> SEQUENCE: 13

Leu Arg Ser Ser Ser Arg Thr Pro Ser Asp Lys Pro Val Ala His Val
 1               5                  10                  15

Val Ala Asn Pro Glu Ala Glu Gly Gln Leu Gln Arg Leu Ser Arg Arg
            20                  25                  30

Ala Asn Ala Leu Leu Ala Asn Gly Val Glu Leu Thr Asp Asn Gln Leu
        35                  40                  45

Lys Val Pro Ser Asp Gly Leu Tyr Leu Ile Tyr Ser Gln Val Leu Phe
    50                  55                  60

Thr Gly Gln Gly Cys Pro Ser Thr His Val Leu Leu Thr His Ala Ile
65                  70                  75                  80

Ser Arg Phe Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Thr Glu Ile Asn Leu Pro Ala Tyr Leu Asp Phe
    130                 135                 140

Ala Glu Ser Gly Gln Val Tyr Phe Gly Ile Ile Ala Leu
145                 150                 155


<210> SEQ ID NO 14
<211> LENGTH: 157
<212> TYPE: PRT
<213> ORGANISM: Canis familiaris

<400> SEQUENCE: 14

Val Leu Ser Ser Ser Arg Thr Pro Ser Asp Lys Pro Val Ala His Val
 1               5                  10                  15

Val Ala Asn Pro Glu Ala Glu Gly Gln Leu Gln Trp Leu Ser Arg Arg
            20                  25                  30

Ala Asn Ala Leu Leu Ala Asn Gly Val Glu Leu Thr Asp Asn Gln Leu
        35                  40                  45

Ile Val Pro Ser Asp Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Phe Ala Val Ser Tyr Gln Thr Lys Val Asn Leu Leu Ser Ala
                85                  90                  95
```

-continued

```
Ile Lys Ser Pro Cys Gln Arg Glu Thr Pro Glu Gly Thr Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Leu Pro Asn Tyr Leu Asp Phe
    130                 135                 140

Ala Glu Ser Gly Gln Val Tyr Phe Gly Ile Ile Ala Leu
145                 150                 155


<210> SEQ ID NO 15
<211> LENGTH: 157
<212> TYPE: PRT
<213> ORGANISM: Ovis aries

<400> SEQUENCE: 15

Leu Arg Ser Ser Ser Gln Ala Ser Asn Asn Lys Pro Val Ala His Val
 1               5                  10                  15

Val Ala Asn Leu Ser Ala Pro Gly Gln Leu Arg Trp Gly Asp Ser Tyr
            20                  25                  30

Ala Asn Ala Leu Met Ala Asn Gly Val Glu Leu Lys Asp Asn Gln Leu
        35                  40                  45

Val Val Pro Thr Asp Gly Leu Tyr Leu Ile Tyr Ser Gln Val Leu Phe
    50                  55                  60

Arg Gly His Gly Cys Pro Ser Thr Pro Leu Phe Leu Thr His Thr Ile
65                  70                  75                  80

Ser Arg Ile Ala Val Ser Tyr Gln Thr Lys Val Asn Ile Leu Ser Ala
                85                  90                  95

Ile Lys Ser Pro Cys His Arg Glu Thr Leu Glu Gly Ala Glu Ala Lys
            100                 105                 110

Pro Trp Tyr Glu Pro Ile Tyr Gln Gly Gly Val Phe Gln Leu Glu Lys
        115                 120                 125

Gly Asp Arg Leu Ser Ala Glu Ile Asn Leu Pro Glu Tyr Leu Asp Tyr
    130                 135                 140

Ala Glu Ser Gly Gln Val Tyr Phe Gly Ile Ile Ala Leu
145                 150                 155


<210> SEQ ID NO 16
<211> LENGTH: 156
<212> TYPE: PRT
<213> ORGANISM: Capra hircus

<400> SEQUENCE: 16

Leu Arg Ser Ser Ser Gln Ala Ser Ser Asn Lys Pro Val Ala His Val
 1               5                  10                  15

Val Ala Asn Ile Ser Ala Pro Gly Gln Leu Arg Trp Gly Asp Ser Tyr
            20                  25                  30

Ala Asn Ala Leu Lys Ala Asn Gly Val Glu Leu Lys Asp Asn Gln Leu
        35                  40                  45

Val Val Pro Thr Asp Gly Leu Tyr Leu Ile Tyr Ser Gln Val Leu Phe
    50                  55                  60

Arg Gly His Gly Cys Pro Ser Thr Pro Leu Phe Leu Thr His Thr Ile
65                  70                  75                  80

Ser Arg Ile Ala Val Ser Tyr Gln Thr Lys Val Asn Ile Leu Ser Ala
                85                  90                  95

Ile Lys Ser Pro Cys His Arg Glu Thr Pro Glu Ala Glu Ala Lys Pro
            100                 105                 110

Trp Tyr Glu Pro Ile Tyr Gln Gly Gly Val Glu Gln Leu Glu Lys Gly
```

```
        115                 120                 125

Asp Arg Leu Ser Ala Glu Ile Asn Gln Pro Glu Tyr Leu Asp Tyr Ala
    130                 135                 140

Glu Ser Gly Gln Val Tyr Phe Gly Ile Ile Ala Leu
145                 150                 155


<210> SEQ ID NO 17
<211> LENGTH: 157
<212> TYPE: PRT
<213> ORGANISM: Equus caballus

<400> SEQUENCE: 17

Leu Arg Ser Ser Ser Arg Thr Pro Ser Asp Lys Pro Val Ala His Val
 1               5                  10                  15

Val Ala Asn Pro Gln Ala Glu Gly Gln Leu Gln Trp Leu Ser Gly Arg
            20                  25                  30

Ala Asn Ala Leu Leu Ala Asn Gly Val Lys Leu Thr Asp Asn Gln Leu
        35                  40                  45

Val Val Pro Leu Asp Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Leu Ala Val Ser Tyr Pro Ser Lys Val Asn Leu Leu Ser Ala
                85                  90                  95

Ile Lys Ser Pro Cys His Thr Glu Ser Pro Glu Gln Ala Glu Ala Lys
            100                 105                 110

Pro Trp Tyr Glu Pro Ile Tyr Leu Gly Gly Val Phe Gln Leu Glu Lys
        115                 120                 125

Gly Asp Gln Leu Ser Ala Glu Ile Asn Gln Pro Asn Tyr Leu Asp Phe
    130                 135                 140

Ala Glu Ser Gly Gln Val Tyr Phe Gly Ile Ile Ala Leu
145                 150                 155


<210> SEQ ID NO 18
<211> LENGTH: 156
<212> TYPE: PRT
<213> ORGANISM: Box taurus

<400> SEQUENCE: 18

Leu Arg Ser Ser Ser Gln Ala Ser Ser Asn Lys Pro Val Ala His Val
 1               5                  10                  15

Val Ala Asp Ile Asn Ser Pro Gly Gln Leu Arg Trp Trp Asp Ser Tyr
            20                  25                  30

Ala Asn Ala Leu Met Ala Asn Gly Val Gln Leu Glu Asp Asn Gln Leu
        35                  40                  45

Val Val Pro Ala Glu Gly Leu Tyr Leu Ile Tyr Ser Gln Val Leu Phe
    50                  55                  60

Arg Gly Gln Gly Cys Pro Pro Pro Pro Val Leu Thr His Thr Ile Ser
65                  70                  75                  80

Arg Ile Ala Val Ser Tyr Gln Thr Lys Val Asn Ile Leu Ser Ala Ile
                85                  90                  95

Lys Ser Pro Cys His Arg Glu Thr Pro Glu Trp Ala Glu Ala Lys Pro
            100                 105                 110

Trp Tyr Glu Pro Ile Tyr Gln Gly Gly Val Phe Gln Leu Glu Lys Asp
        115                 120                 125

Asp Arg Leu Ser Ala Glu Ile Asn Leu Pro Asp Tyr Leu Asp Tyr Ala
    130                 135                 140
```

```
Glu Ser Gly Gln Val Tyr Phe Gly Ile Ile Ala Leu
145                 150                 155


<210> SEQ ID NO 19
<211> LENGTH: 156
<212> TYPE: PRT
<213> ORGANISM: Sus scrofa

<400> SEQUENCE: 19

Leu Arg Ser Ser Ser Gln Thr Ser Asp Lys Pro Val Ala His Val Val
 1               5                  10                  15

Ala Asn Val Lys Ala Glu Gly Gln Leu Gln Trp Gln Ser Gly Tyr Ala
            20                  25                  30

Asn Ala Leu Leu Ala Asn Gly Val Lys Leu Lys Asp Asn Gln Leu Val
        35                  40                  45

Val Pro Thr Asp Gly Leu Tyr Leu Ile Tyr Ser Gln Val Leu Phe Arg
    50                  55                  60

Gly Gln Gly Cys Pro Ser Thr Asn Val Phe Leu Thr His Thr Ile Ser
65                  70                  75                  80

Arg Ile Ala Val Ser Tyr Gln Thr Lys Val Asn Leu Leu Ser Ala Ile
                85                  90                  95

Lys Ser Pro Cys Gln Arg Glu Thr Pro Glu Gly Ala Glu Ala Lys Pro
            100                 105                 110

Trp Tyr Glu Pro Ile Tyr Leu Gly Gly Val Phe Gln Leu Glu Lys Asp
        115                 120                 125

Asp Arg Leu Ser Ala Glu Ile Asn Leu Pro Asp Tyr Leu Asp Phe Ala
    130                 135                 140

Glu Ser Gly Gln Val Tyr Phe Gly Ile Ile Ala Leu
145                 150                 155


<210> SEQ ID NO 20
<211> LENGTH: 8
<212> TYPE: PRT
<213> ORGANISM: Homo sapiens

<400> SEQUENCE: 20

Leu Asn Arg Arg Ala Asn Ala Leu
 1               5


<210> SEQ ID NO 21
<211> LENGTH: 8
<212> TYPE: PRT
<213> ORGANISM: Homo sapiens

<400> SEQUENCE: 21

Ala Val Ser Tyr Gln Thr Lys Val
 1               5


<210> SEQ ID NO 22
<211> LENGTH: 6
<212> TYPE: PRT
<213> ORGANISM: Homo sapiens

<400> SEQUENCE: 22

Asp Phe Ala Glu Ser Gly
 1               5


<210> SEQ ID NO 23
<211> LENGTH: 5
<212> TYPE: PRT
<213> ORGANISM: Artificial Sequence
```

<220> FEATURE:
<223> OTHER INFORMATION: Chemically synthesized variant of TNFalpha
mutein consensus sequence

<400> SEQUENCE: 23

His Gln Val Glu Glu
1 5

<210> SEQ ID NO 24
<211> LENGTH: 5
<212> TYPE: PRT
<213> ORGANISM: Artificial Sequence
<220> FEATURE:
<223> OTHER INFORMATION: Chemically synthesized variant of TNFalpha
mutein consensus sequence

<400> SEQUENCE: 24

His Gln Ala Glu Glu
1 5

<210> SEQ ID NO 25
<211> LENGTH: 5
<212> TYPE: PRT
<213> ORGANISM: Artificial Sequence
<220> FEATURE:
<223> OTHER INFORMATION: Chemically synthesized variant of TNFalpha
mutein consensus sequence

<400> SEQUENCE: 25

Pro Gln Val Glu Glu
1 5

<210> SEQ ID NO 26
<211> LENGTH: 5
<212> TYPE: PRT
<213> ORGANISM: Artificial Sequence
<220> FEATURE:
<223> OTHER INFORMATION: Chemically synthesized variant of TNFalpha
mutein consensus sequence

<400> SEQUENCE: 26

Pro Glu Ala Glu Gly
1 5

<210> SEQ ID NO 27
<211> LENGTH: 5
<212> TYPE: PRT
<213> ORGANISM: Artificial Sequence
<220> FEATURE:
<223> OTHER INFORMATION: Chemically synthesized variant of TNFalpha
mutein consensus sequence

<400> SEQUENCE: 27

Leu Ser Ala Pro Gly
1 5

<210> SEQ ID NO 28
<211> LENGTH: 5
<212> TYPE: PRT
<213> ORGANISM: Artificial Sequence
<220> FEATURE:
<223> OTHER INFORMATION: Chemically synthesized variant of TNFalpha
mutein consensus sequence

<400> SEQUENCE: 28

Ile Ser Ala Pro Gly
1 5

<210> SEQ ID NO 29
<211> LENGTH: 5
<212> TYPE: PRT
<213> ORGANISM: Artificial Sequence
<220> FEATURE:
<223> OTHER INFORMATION: Chemically synthesized variant of TNFalpha mutein consensus sequence

<400> SEQUENCE: 29

Pro Gln Ala Glu Gly
1 5

<210> SEQ ID NO 30
<211> LENGTH: 5
<212> TYPE: PRT
<213> ORGANISM: Artificial Sequence
<220> FEATURE:
<223> OTHER INFORMATION: Chemically synthesized variant of TNFalpha mutein consensus sequence

<400> SEQUENCE: 30

Ile Asn Ser Pro Gly
1 5

<210> SEQ ID NO 31
<211> LENGTH: 5
<212> TYPE: PRT
<213> ORGANISM: Artificial Sequence
<220> FEATURE:
<223> OTHER INFORMATION: Chemically synthesized variant of TNFalpha mutein consensus sequence

<400> SEQUENCE: 31

Val Lys Ala Glu Gly
1 5

<210> SEQ ID NO 32
<211> LENGTH: 4
<212> TYPE: PRT
<213> ORGANISM: Artificial Sequence
<220> FEATURE:
<223> OTHER INFORMATION: Chemically synthesized variant of TNFalpha mutein consensus sequence

<400> SEQUENCE: 32

Leu Ser Gln Arg
1

<210> SEQ ID NO 33
<211> LENGTH: 4
<212> TYPE: PRT
<213> ORGANISM: Artificial Sequence
<220> FEATURE:
<223> OTHER INFORMATION: Chemically synthesized variant of TNFalpha mutein consensus sequence

<400> SEQUENCE: 33

Leu Ser Arg Arg
1

<210> SEQ ID NO 34
<211> LENGTH: 4
<212> TYPE: PRT
<213> ORGANISM: Artificial Sequence
<220> FEATURE:
<223> OTHER INFORMATION: Chemically synthesized variant of TNFalpha mutein consensus sequence

<400> SEQUENCE: 34

Gly Asp Ser Tyr
1

<210> SEQ ID NO 35
<211> LENGTH: 4
<212> TYPE: PRT
<213> ORGANISM: Artificial Sequence
<220> FEATURE:
<223> OTHER INFORMATION: Chemically synthesized variant of TNFalpha mutein consensus sequence

<400> SEQUENCE: 35

Leu Ser Gly Arg
1

<210> SEQ ID NO 36
<211> LENGTH: 4
<212> TYPE: PRT
<213> ORGANISM: Artificial Sequence
<220> FEATURE:
<223> OTHER INFORMATION: Chemically synthesized variant of TNFalpha mutein consensus sequence

<400> SEQUENCE: 36

Trp Asp Ser Tyr
1

<210> SEQ ID NO 37
<211> LENGTH: 4
<212> TYPE: PRT
<213> ORGANISM: Artificial Sequence
<220> FEATURE:
<223> OTHER INFORMATION: Chemically synthesized variant of TNFalpha mutein consensus sequence

<400> SEQUENCE: 37

Gln Ser Gly Tyr
1

<210> SEQ ID NO 38
<211> LENGTH: 4
<212> TYPE: PRT
<213> ORGANISM: Artificial Sequence
<220> FEATURE:
<223> OTHER INFORMATION: Chemically synthesized variant of TNFalpha mutein consensus sequence

<400> SEQUENCE: 38

Leu Asn Arg Arg
1

<210> SEQ ID NO 39
<211> LENGTH: 4
<212> TYPE: PRT
<213> ORGANISM: Artificial Sequence
<220> FEATURE:
<223> OTHER INFORMATION: Chemically synthesized variant of TNFalpha mutein consensus sequence

<400> SEQUENCE: 39

Asp Val Val Leu
1

<210> SEQ ID NO 40
<211> LENGTH: 4
<212> TYPE: PRT
<213> ORGANISM: Artificial Sequence
<220> FEATURE:
<223> OTHER INFORMATION: Chemically synthesized variant of TNFalpha mutein consensus sequence

<400> SEQUENCE: 40

Asp Tyr Val Leu
1

<210> SEQ ID NO 41
<211> LENGTH: 4
<212> TYPE: PRT
<213> ORGANISM: Artificial Sequence
<220> FEATURE:
<223> OTHER INFORMATION: Chemically synthesized variant of TNFalpha
mutein consensus sequence

<400> SEQUENCE: 41

Ser Tyr Val Leu
1

<210> SEQ ID NO 42
<211> LENGTH: 4
<212> TYPE: PRT
<213> ORGANISM: Artificial Sequence
<220> FEATURE:
<223> OTHER INFORMATION: Chemically synthesized variant of TNFalpha
mutein consensus sequence

<400> SEQUENCE: 42

Pro Pro Pro Val
1

<210> SEQ ID NO 43
<211> LENGTH: 5
<212> TYPE: PRT
<213> ORGANISM: Artificial Sequence
<220> FEATURE:
<223> OTHER INFORMATION: Chemically synthesized variant of TNFalpha
mutein consensus sequence

<400> SEQUENCE: 43

Ser Thr His Val Leu
1 5

<210> SEQ ID NO 44
<211> LENGTH: 5
<212> TYPE: PRT
<213> ORGANISM: Artificial Sequence
<220> FEATURE:
<223> OTHER INFORMATION: Chemically synthesized variant of TNFalpha
mutein consensus sequence

<400> SEQUENCE: 44

Ser Thr Pro Leu Phe
1 5

<210> SEQ ID NO 45
<211> LENGTH: 5
<212> TYPE: PRT
<213> ORGANISM: Artificial Sequence
<220> FEATURE:
<223> OTHER INFORMATION: Chemically synthesized variant of TNFalpha
mutein consensus sequence

<400> SEQUENCE: 45

Ser Thr His Val Leu
1 5

<210> SEQ ID NO 46
<211> LENGTH: 5

-continued

```
<212> TYPE: PRT
<213> ORGANISM: Artificial Sequence
<220> FEATURE:
<223> OTHER INFORMATION: Chemically synthesized variant of TNFalpha
      mutein consensus sequence

<400> SEQUENCE: 46

Ser Thr Asn Val Phe
 1               5
```

IMMOBILIZED TUMOR NECROSIS FACTOR-α MUTEINS FOR ENHANCING IMMUNE RESPONSE IN MAMMALS

This application is a continuation application of U.S. application Ser. No. 11/234,057, filed on Sep. 22, 2005 now abandoned, the contents of which are herein incorporated by reference in their entirety.

This invention relates generally to the field of immunotherapy and, more specifically, to methods for enhancing host immune responses.

BACKGROUND OF THE INVENTION

The immune system of mammals has evolved to protect the host against the growth and proliferation of potentially deleterious agents. These agents include infectious microorganisms such as bacteria, viruses, fungi, and parasites which exist in the environment and which, upon introduction to the body of the host, can induce varied pathological conditions. Other pathological conditions may derive from agents not acquired from the environment, but rather which arise spontaneously within the body of the host. The best examples are the numerous malignancies known to occur in mammals. Ideally, the presence of these deleterious agents in a host triggers the mobilization of the immune system to effect the destruction of the agent and, thus, restore the sanctity of the host environment.

The destruction of pathogenic agents by the immune system involves a variety of effector mechanisms which can be grouped generally into two categories: innate and specific immunity. The first line of defense is mediated by the mechanisms of innate immunity. Innate immunity does not discriminate among the myriad agents that might gain entry into the host's body. Rather, it responds in a generalized manner that employs the inflammatory response, phagocytes, and plasma-borne components such as complement and interferons. In contrast, specific immunity does discriminate among pathogenic agents. Specific immunity is mediated by B and T lymphocytes and it serves, in large, part, to amplify and focus the effector mechanisms of innate immunity.

The elaboration of an effective immune response requires contributions from both innate and specific immune mechanisms. The function of each of these arms of the immune system individually, as well as their interaction with each other, is carefully coordinated, both in a temporal/spatial manner and in terms of the particular cell types that participate. This coordination results from the actions of a number of soluble immunostimulatory mediators or "immune system stimulators" (reviewed in, Trinchieri et al., *J. Cell Biochem.* 53:301-308 (1993)). Certain of these immune system stimulators initiate and perpetuate the inflammatory response and the attendant systemic sequelae. Examples of these include, but are not limited to, the proinflammatory mediators tumor necrosis factors α and β, interleukin-1, interleukin-6, interleukin-8, interferon-γ, and the chemokines RANTES, macrophage inflammatory proteins 1-α and 1-β and macrophage chemotactic and activating factor. Other immune system stimulators facilitate interactions between B and T lymphocytes of specific immunity. Examples of these include, but are not limited to, interleukin-2, interleukin-4, interleukin-5, interleukin-6, and interferon-γ. Still other immune system stimulators mediate bidirectional communication between specific immunity and innate immunity. Examples of these include, but are not limited to, interferon-7, interleukin-1, tumor necrosis factors α and β, and interleukin-12. All of these immune system stimulators exert their effects by binding the specific receptors on the surface of host cells, resulting in the delivery of intercellular signals that alter the function of the target cell. Cooperatively, these mediators stimulate the activation and proliferation of immune cells, recruit them to particular anatomical sites, and permit their collaboration in the elimination of the offending agent. The immune response induced in any individual is determined by the particular complement of immune system stimulators produced, and by the relative abundance of each.

In contrast to the immune system stimulators described above, the immune system has evolved other soluble mediators that serve to inhibit immune responses (reviewed in Arend, *Adv. Int. Med.* 40:365-394 (1995)). These "immune system inhibitors" provide the immune system with the ability to dampen responses in order to prevent the establishment of a chronic inflammatory state with the potential to damage the host's tissues. Regulation of host immune function by immune system inhibitors is accomplished through a variety of mechanisms as described below.

First, certain immune system inhibitors bind directly to immune system stimulators and, thus, prevent them from binding to plasma membrane receptors on host cells. Examples of these types of immune system inhibitors include, but are not limited to, the soluble receptors for tumor necrosis factors α and β, interferon-γ, interleukin-1, interleukin-2, interleukin-4, interleukin-6, and interleukin-7.

Second, certain immune system inhibitors antagonize the binding of immune system stimulators to their receptors. By way of example, interleukin-1 receptor antagonist is known to bind to the interleukin-1 membrane receptor. It does not deliver activation signals to the target cell but, by virtue of occupying the interleukin-1 membrane receptor, blocks the effects of interleukin-1.

Third, particular immune system inhibitors exert their effects by binding to receptors on host cells and signaling a decrease in their production of immune system stimulators. Examples include, but are not limited to, interferon-β, which decreases the production of two key proinflammatory mediators, tumor necrosis factor α and interleukin-1 (Coclet-Ninin et al., *Eur. Cytokine Network* 8:345-349 (1997)), and interleukin-10, which suppresses the development of cell-mediated immune responses by inhibiting the production of the immune system stimulator, interleukin-12 (D'Andrea et al., *J. Exp. Med.* 178:1041-1048 (1993)). In addition to decreasing the production of immune system stimulators, certain immune system inhibitors also enhance the production of other immune system inhibitors. By way of example, interferon-$\alpha_{2b}$ inhibits interleukin-1 and tumor necrosis factor α production and increases the production of the corresponding immune system inhibitors, interleukin-1 receptor antagonist and soluble receptors for tumor necrosis factors α and β (Dinarello, *Sem. in Oncol.* 24(3 Suppl. 9):81-93 (1997).

Fourth, certain immune system inhibitors act directly on immune cells, inhibiting their proliferation and function, thereby decreasing the vigor of the immune response. By way of example, transforming growth factor-β inhibits a variety of immune cells and significantly limits inflammation and cell-mediated immune responses (reviewed in Letterio and Roberts, *Ann. Rev. Immunol.* 16:137-161 (1998)). Collectively, these various immunosuppressive mechanisms are intended to regulate the immune response, both quantitatively and qualitatively, to minimize the potential for collateral damage to the host's own tissues.

In addition to the inhibitors produced by the host's immune system for self-regulation, other immune system inhibitors are produced by infectious microorganisms. For example, many viruses produce molecules which are viral homologues of host immune system inhibitors (reviewed in Spriggs, *Ann. Rev. Immunol.* 14:101-130 (1996)). These include homologues of host complement inhibitors, interleukin-10, and soluble receptors for interleukin-1, tumor necrosis factors α and β, and interferons α, β and γ. Similarly, helminthic parasites produce homologues of host immune system inhibitors (reviewed in Riffkin et al., *Immunol. Cell Biol.* 74:564-574 (1996)), and several bacterial genera are known to produce immunosuppressive products (reviewed in, Reimann et al., *Scand. J. Immunol.* 31:543-546 (1990)). All of these immune system inhibitors serve to suppress the immune response during the initial stages of infection, to provide advantage to the microbe, and to enhance the virulence and chronicity of the infection.

A role for host-derived immune system inhibitors in chronic disease also has been established. In the majority of cases, this reflects a polarized T cell response during the initial infection, wherein the production of immunosuppressive mediators (i.e., interleukin-4, interleukin-10, and/or transforming growth factor-β) dominates over the production of immunostimulatory mediators (i.e., interleukin-2, interferon-γ, and/or tumor necrosis factor β) (reviewed in Lucey et al., *Clin. Micro. Rev.* 9:532-562 (1996)). Overproduction of immunosuppressive mediators of this type has been shown to produce chronic, non-healing pathologies in a number of medically important diseases. These include, but are not limited to, diseases resulting from infection with: 1) the parasites, *Plasmodium falciparum* (Sarthou et al., *Infect. Immun.* 65:3271-3276 (1997)), *Trypanosoma cruzi* (reviewed in Laucella et al., *Revista Argentina de Microbiolgia* 28:99-109 (1996)), *Leishmania major* (reviewed in Etges and Muller, *J. Mol. Med.* 76:372-390 (1998)), and certain helminths (Riffkin et al., supra); 2) the intracellular bacteria, *Mycobacterium tuberculosis* (Baliko et al., *FEMS Immunol. Med. Micro.* 22:199-204 (1998)), *Mycobacterium avium* (Bermudez and Champsi, *Infect. Immun.* 61:3093-3097 (1993)), *Mycobacterium leprae* (Sieling et al., *J. Immunol.* 150:5501-5510 (1993)), *Mycobacterium bovis* (Kaufmann et al., *Ciba Fdn. Symp.* 195:123-132 (1995)), *Brucella abortus* (Fernandes and Baldwin, *Infect. Immun.* 63:1130-1133 (1995)), and *Listeria monocytogenes* (Blauer et al., *J. Interferon Cytokine Res.* 15:105-114 (1995)), and, 3) intracellular fungus, *Candida albicans* (reviewed in Romani et al., *Immunol. Res.* 14:148-162 (1995)). The inability to spontaneously resolve infection is influenced by other host-derived immune system inhibitors as well. By way of example, interleukin-1 receptor antagonist and the soluble receptors for tumor necrosis factors α and β are produced in response to interleukin-1 and tumor necrosis factor α and/or β production driven by the presence of numerous infectious agents. Examples include, but are not limited to, infections by *Plasmodium falciparum* (Jakobsen et al., *Infect. Immun.* 66:1654-1659 (1998); Sarthou et al., supra), *Mycobacterium tuberculosis* (Balcewicz-Sablinska et al., *J. Immunol.* 161:2636-2641 (1998)), and *Mycobacterium avium* (Eriks and Emerson, *Infect. Immun.* 65:2100-2106 (1997)). In cases where the production of any of the aforementioned immune system inhibitors, either individually or in combination, dampens or otherwise alters immune responsiveness before the elimination of the pathogenic agent, a chronic infection may result.

In addition to this role in infectious disease, host-derived immune system inhibitors contribute also to chronic malignant disease. Compelling evidence is provided by studies of soluble tumor necrosis factor receptor Type I (sTNFRI) in cancer patients. Nanomolar concentrations of sTNFRI are synthesized by a variety of activated immune cells in cancer patients and, in many cases, by the tumors themselves (Aderka et al., *Cancer Res.* 51:5602-5607 (1991); Adolf and Apfler, *J. Immunol. Meth.* 143:127-136 (1991)). In addition, circulating sTNFRI levels often are elevated significantly in cancer patients (Aderka et al., supra; Kalmanti et al., *Int. J. Hematol.* 57:147-152 (1993); Elsasser-Beile et al., *Tumor Biol.* 15:17-24 (1994); Gadducci et al., *Anticancer Res.* 16:3125-3128 (1996); Digel et al., *J. Clin. Invest.* 89:1690-1693 (1992)), decline during remission and increase during advanced stages of tumor development (Aderka et al., supra; Kalmanti et al., supra; Elsasser-Beile et al., supra; Gadducci et al., supra) and, when present at high levels, correlate with poorer treatment outcomes (Aderka et al., supra). These observations suggest that sTNFRI aids tumor survival by inhibiting anti-tumor immune mechanisms which employ tumor necrosis factors α and/or β (TNF), and they argue favorably for the clinical manipulation of sTNFRI levels as a therapeutic strategy for cancer.

Direct evidence that the removal of immune system inhibitors provides clinical benefit derives from the evaluation of Ultrapheresis, a promising experimental cancer therapy (Lentz, *J. Biol. Response Modif.* 8:511-527 (1989); Lentz, *Ther. Apheresis* 3:40-49 (1999); Lentz, *Jpn. J. Apheresis* 16:107-114 (1997)). Ultrapheresis involves extracorporeal fractionation of plasma components by ultrafiltration. Ultrapheresis selectively removes plasma components within a defined molecular size range, and it has been shown to provide significant clinical advantage to patients presenting with a variety of tumor types. Ultrapheresis induces pronounced inflammation at tumor sites, often in less than one hour post-initiation. This rapidity suggests a role for preformed chemical and/or cellular mediators in the elaboration of this inflammatory response, and it reflects the removal of naturally occurring plasma inhibitors of that response. Indeed, immune system inhibitors of TNF α and β, interleukin-1, and interleukin-6 are removed by Ultrapheresis (Lentz, *Ther. Apheresis* 3:40-49 (1999)). Notably, the removal of sTNFRI has been correlated with the observed clinical responses (Lentz, *Ther. Apheresis* 3:40-49 (1999); Lentz, *Jpn. J. Apheresis* 16:107-114 (1997)).

Ultrapheresis is in direct contrast to more traditional approaches which have endeavored to boost immunity through the addition of immune system stimulators. Preeminent among these has been the infusion of supraphysiological levels of TNF (Sidhu and Bollon, *Pharmacol. Ther.* 57:79-128 (1993)); and of interleukin-2 (Maas et al., *Cancer Immunol. Immunother.* 36:141-148 (1993)), which indirectly stimulates the production of TNF. These therapies have enjoyed limited success (Sidhu and Bollon, supra, Maas et al., supra) due to the fact: 1) that at the levels employed they proved extremely toxic; and 2) that each increases the plasma levels of the immune system inhibitor, sTNFRI (Lantz et al., *Cytokine* 2:402-406 (1990); Miles et al., *Brit. J. Cancer* 66:1195-1199 (1992)). Together, these observations support the utility of Ultrapheresis as a biotherapeutic approach to cancer—one which involves the removal of immune system inhibitors, rather than the addition of immune system stimulators.

Although Ultrapheresis provides advantages over traditional therapeutic approaches, there are certain drawback that limit its clinical usefulness. Not only are immune system inhibitors removed by Ultrapheresis, but other plasma components, including beneficial ones, are removed since the discrimination between removed and retained plasma components is based solely on molecular size. An additional drawback to Ultrapheresis is the significant loss of circulatory volume during treatment, which must be offset by the infusion of replacement fluid. The most effective replacement fluid is an ultrafiltrate produced, in an identical manner, from the plasma of non-tumor bearing donors. A typical treatment regimen (15 treatments, each with the removal of approximately 7 liters of ultrafiltrate) requires over 200 liters of donor plasma for the production of replacement fluid. The chronic shortage of donor plasma, combined with the risks of infection by human immunodeficiency virus, hepatitis A, B, and C or other etiologic agents, represents a severe impediment to the widespread implementation of Ultrapheresis.

Because of the beneficial effects associated with the removal of immune system inhibitors, there exists a need for methods which can be used to specifically deplete those inhibitors from circulation. Such methods ideally should be specific and not remove other circulatory components, and they should not result in any significant loss of circulatory volume. The present invention satisfies these needs and provides related advantages as well.

SUMMARY OF INVENTION

The present invention provides a method for stimulating immune responses in a mammal through the depletion of immune system inhibitors such as soluble TNF receptors present in the circulation of the mammal. The depletion of immune system inhibitors such as soluble TNF receptors can be effected by removing biological fluids from the mammal and contacting these biological fluids with a binding partner capable of selectively binding to the targeted immune system inhibitor, for example, TNFα muteins.

Binding partners useful in these methods are TNFα muteins having specificity for soluble TNF receptors. Moreover, mixtures of TNFα muteins having specificity for one or more soluble TNF receptors can be used.

In a particularly useful embodiment, the binding partner, such as a TNFα mutein, is immobilized previously on a solid support to create an "absorbent matrix" (FIG. 1). The exposure of biological fluids to such an absorbent matrix will permit binding by the immune system inhibitor such as soluble TNF receptor, thus, effecting a decrease in its abundance in the biological fluids. The treated biological fluid can be returned to the patient. The total volume of biological fluid to be treated and the treatment rate are parameters individualized for each patient, guided by the induction of vigorous immune responses while minimizing toxicity. The solid support (i.e., inert medium) can be composed of any material useful for such purpose, including, for example, hollow fibers, cellulose-based fibers, synthetic fibers, flat or pleated membranes, silica-based particles, macroporous beads, and the like.

In another embodiment, the binding partner such as TNFα mutein can be mixed with the biological fluid in a "stirred reactor" (FIG. 2). The binding partner-immune system inhibitor complex then can be removed by mechanical or by chemical or biological means, and the altered biological fluid can be returned to the patient.

The present invention also provides apparatus incorporating either the absorbent matrix or the stirred reactor.

BRIEF DESCRIPTION OF THE FIGURES

FIG. 3A shows an alignment of TNFα sequences from various mammalian species (mouse, SEQ ID NO:10; rat, SEQ ID NO:11; rabbit, SEQ ID NO:12; cat, SEQ ID NO:13; dog, SEQ ID NO:14; sheep, SEQ ID NO:15; goat, SEQ ID NO:16; horse, SEQ ID NO:17; cow, SEQ ID NO:18; pig, SEQ ID NO:19; human, SEQ ID NO:2). The top sequence shows the conserved amino acids across the shown species (SEQ ID NO:1) (completely conserved or with one exception). Non-conserved amino acids are indicated by "." (taken from Van Ostade et al., *Prot. Eng.* 7:5-22 (1994), which is incorporated herein by reference). FIG. 3B shows an alignment of the conserved TNFα sequence with human TNFα and six representative TNFα muteins, designated mutein 1 (SEQ ID NO:3), mutein 2 (SEQ ID NO:4), mutein 3 (SEQ ID NO:5), mutein 4 (SEQ ID NO:6), mutein 5 (SEQ ID NO:7), and mutein 6 (SEQ ID NO:8). The four muteins differ from the human sequence by single amino acid substitutions, indicated with bold and underline. FIG. 3C shows a representative consensus TNFα: sequence (SEQ ID NO:9).

DETAILED DESCRIPTION OF THE INVENTION

Figure 1:
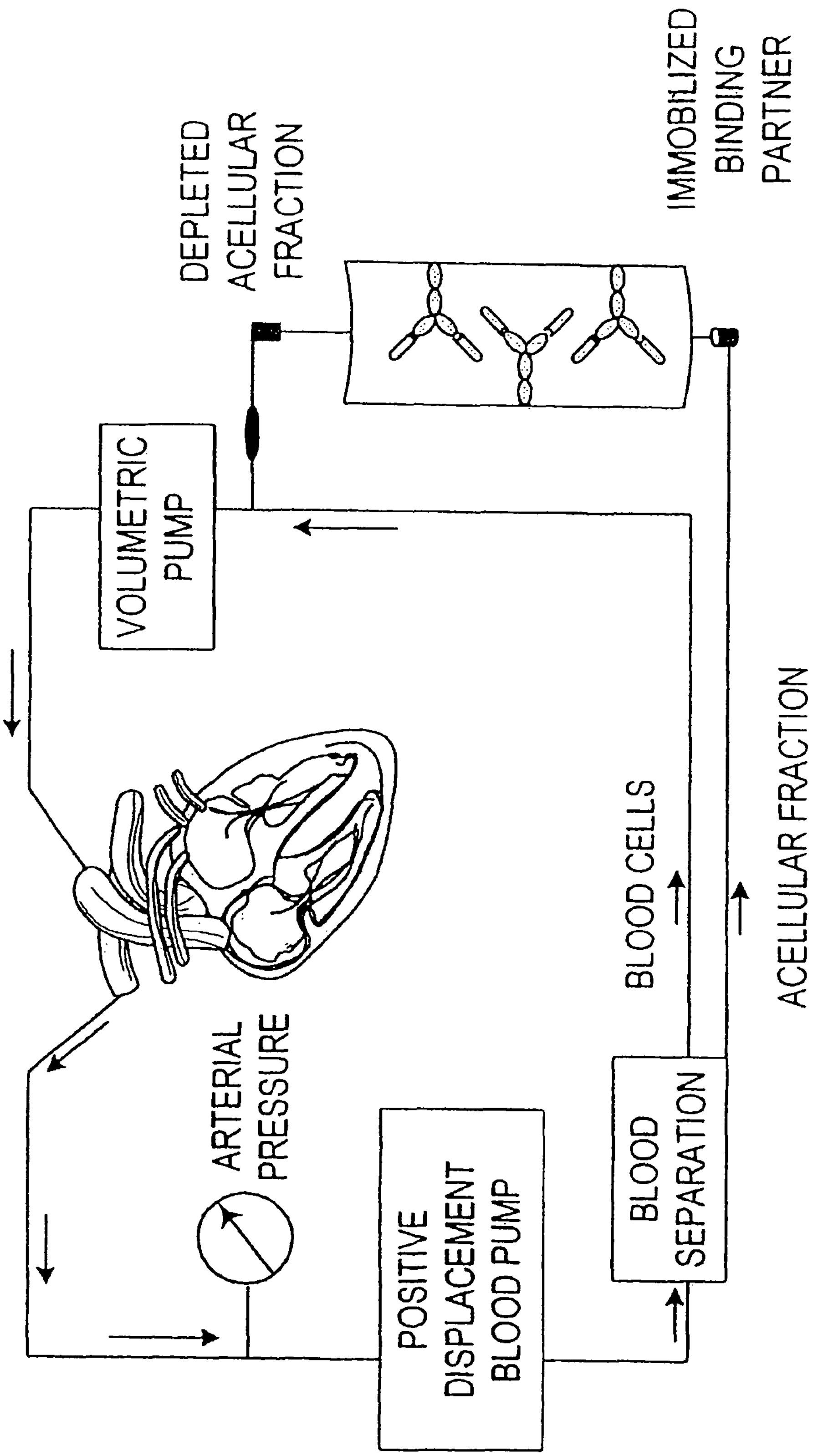
FIG. 1 schematically illustrates an "absorbent matrix" configuration of an embodiment of the invention. In this example, blood is removed from the patient and separated into a cellular and an acellular component, or factions thereof. The acellular component, or fractions thereof, is exposed to the absorbent matrix to effect the binding and, thus, depletion of a targeted immune system inhibitor such as soluble tumor necrosis factor (TNF) receptor. The altered acellular component, or fractions thereof, then is returned contemporaneously to the patient.

The present invention provides methods to reduce the levels of immune system inhibitors such as soluble TNF receptors in the circulation of a host mammal, thereby potentiating an immune response capable of resolving a pathological condition or decreasing the severity of a pathological condition. By enhancing the magnitude of the host's immune response, the methods of the present invention avoid the problems associated with the repeated administration of chemotherapeutic agents which often have undesirable side effects, for example, chemotherapeutic agents used in treating cancer.

The methods of the present invention generally are accomplished by: (a) obtaining a biological fluid from a mammal having a pathological condition; (b) contacting the biological fluid with a TNFα mutein binding partner capable of selectively binding to a targeted immune system inhibitor such as soluble TNF receptor to produce an altered biological fluid having a reduced amount of the targeted immune system inhibitor; and, thereafter (c) administering the altered biological fluid to the mammal.

As used herein, the term "immune system stimulator" refers to soluble mediators that increase the magnitude of an immune response, or which encourage the development of particular immune mechanisms that are more effective in resolving a specific pathological condition. Examples of immune system stimulators include, but are not limited to, the proinflammatory mediators tumor necrosis factors α and β, interleukin-1, interleukin-2, interleukin-4, interleukin-5, interleukin-6, interleukin-8, interleukin-12, interferon-γ, interferon-7; and the chemokines RANTES, macrophage inflammatory proteins 1-α and 1-β and macrophage chemotactic and activating factor, as discussed above.

As used herein, the term "immune system inhibitor" refers to a soluble mediator that decreases the magnitude of an immune response, or which discourages the development of particular immune mechanisms that are more effective in resolving a specific pathological condition, or which encourages the development of particular immune mechanisms that are less effective in resolving a specific pathological condition. Examples of host-derived immune system inhibitors include interleukin-1 receptor antagonist, transforming growth factor-β, interleukin-4, interleukin-10, or the soluble receptors for interleukin-1, interleukin-2, interleukin-4, interleukin-6, interleukin-7, interferon-γ and tumor necrosis factors α and β. In a particular embodiment of the present invention, the immune system inhibitor is soluble TNF receptor Type I (sTNFRI) or Type II (sTNFRII). Immune system inhibitors produced by microorganisms are also potential targets including, for example, soluble receptors for tumor necrosis factor α and β. As used herein, the term "targeted" immune system inhibitor refers to that inhibitor, or collection of inhibitors, which is to be removed from the biological fluid by a method of the invention, for example, sTNFRI and/or sTNFRII.

As used herein, the term "soluble TNF receptor" refers to a soluble form of a receptor for TNFα and TNFβ. Two forms of TNF receptor have been identified, type I receptor (TNFRI), also known as TNF-R55, and type II receptor (TNFRII), also known as TNF-R75, both of which are membrane proteins that bind to TNFα and TNFβ and mediate intracellular signaling. Both of these receptors also occur in a soluble form. The soluble form of TNF receptor functions as an immune system inhibitor, as discussed above. As used herein, a soluble TNF receptor includes at least one of the soluble forms of TNFRI and TNFRII or any other type of TNF receptor. It is understood that, in the methods of the invention, the methods can be used to remove one or both types of TNF receptor depending on whether the TNFα mutein or plurality of muteins used in the method binds to one or both types of receptors.

As used herein, the term "mammal" can be a human or a non-human animal, such as dog, cat, horse, cattle, pig, sheep, non-human primate, mouse, rat, rabbit, or other mammals, for example. The term "patient" is used synonymously with the term "mammal" in describing the invention.

As used herein, the term "pathological condition" refers to any condition where the persistence, within a host, of an agent, immunologically distinct from the host, is a component of or contributes to a disease state. Examples of such pathological conditions include, but are not limited to those resulting from persistent viral, bacterial, parasitic, and fungal infections, and cancer. Among individuals exhibiting such chronic diseases, those in whom the levels of immune system inhibitors are elevated are particularly suitable for the treatment of the invention. Plasma levels of immune system inhibitors can be determined using methods well known in the art (see, for example, Adolf and Apfler, supra, 1991). Those skilled in the art readily can determine pathological conditions that would benefit from the depletion of immune system inhibitors according to the present methods.

As used herein, the term "biological fluid" refers to a bodily fluid obtained from a mammal, for example, blood, including whole blood, plasma, serum, lymphatic fluid, or other types of bodily fluids. If desired, the biological fluid can be processed or fractionated, for example, to obtain an acellular component. As it relates to the present invention, the term "acellular biological fluid" refers to the acellular component of the circulatory system including plasma, serum, lymphatic fluid, or fractions thereof. The biological fluids can be removed from the mammal by any means known to those skilled in the art, including, for example, conventional apheresis methods (see, *Apheresis: Principles and Practice*, McLeod, Price, and Drew, eds., AABB Press, Bethesda, Md. (1997)). The amount of biological fluid to be extracted from a mammal at a given time will depend on a number of factors, including the age and weight of the host mammal and the volume required to achieve therapeutic benefit. As an initial guideline, one plasma volume (approximately 3-5 liters in an adult human) can be removed and, thereafter, depleted of the targeted immune system inhibitor according to the present methods.

As used herein, the term "selectively binds" means that a molecule binds to one type of target molecule, but not substantially to other types of molecules. The term "specifically binds" is used interchangeably herein with "selectively binds."

As used herein, the term "binding partner" is intended to include any molecule chosen for its ability to selectively bind to the targeted immune system inhibitor. The binding partner can be one which naturally binds the targeted immune system inhibitor. For example, tumor necrosis factor α or β can be used as a binding partner for sTNFRI. Alternatively, other binding partners, chosen for their ability to selectively bind to the targeted immune system inhibitor, can be used. Those include fragments of the natural binding partner, polyclonal or monoclonal antibody preparations or fragments thereof, or synthetic peptides. In a particular embodiment of the present invention, the binding partner is a TNFα mutein.

As used herein, the term "TNFα mutein" refers to a TNFα variant having one or more amino acid substitutions relative to a parent sequence and retaining specific binding activity for a TNF receptor. Generally, the muteins of the present invention have a single amino acid substitution relative to a parent sequence. Exemplary TNFα muteins include the human TNFα muteins designated muteins 1, 2, 3, 4, 5 and 6 (see FIG. 3B), which are derived from human TNFα but have a single amino acid substitution relative to the wild type sequence, as discussed below. It is understood that analogous muteins of species other than human are similarly included, for example, muteins analogous to muteins 1, 2, 3, 4, 5 or 6 in the other mammalian species shown in FIG. 3A, or other mammalian species. These and other muteins, as described in more detail below, are included within the meaning of a TNFα mutein of the invention.

The present invention provides compositions and method for stimulating or enhancing an immune response in a mammal. The invention advantageously uses ligands that bind to immune system inhibitors to counterbalance the dampening effect of immune system inhibitors on the immune response.

Such ligands, also referred to herein as "binding partners," can be attached to a solid support to allow the removal of an immune system inhibitor from a biological fluid.

A binding partner particularly useful in the present invention is a ligand that binds with high affinity to an immune system inhibitor, for example, soluble TNF receptor and in particular sTNFRI. Another useful characteristic of a binding partner is a lack of direct toxicity. For example, a binding partner lacking TNF agonist activity is particularly useful. Generally, even when a ligand such as a binding partner is covalently bound to a solid support, a certain percentage of the bound ligand will leach from the support, for example, via chemical reactions that break down the covalent linkage or protease activity present in a biological fluid. In such a case, the ligand will leach into the biological fluid being processed and, thus, be returned to the patient. Therefore, it is advantageous to use a ligand that has affinity for an immune system inhibitor but has decreased ability to stimulate a biological response, that is, has decreased or low agonist activity. In this case, even if some of the ligand leaches into the processed biological fluid, the ligand would still exhibit low biological activity with respect to membrane receptor signaling when reintroduced into the patient.

Yet another useful characteristic of a binding partner is a lack of indirect toxicity, for example, immunogenicity. As discussed above, it is common for a bound ligand to leach from a matrix, resulting in the ligand being present in the processed biological fluid. Because the biological fluid is returned to the patient, this results in the introduction of a low level of the ligand to the patient. If the ligand is immunogenic, an immune response against the ligand can be stimulated, resulting in undesirable immune responses, particularly in a patient in which the process is being repeated. Therefore, a ligand having low immunogenicity would minimize any undesirable immune responses against the ligand. As disclosed herein, a particularly useful ligand to be used as a binding partner of the invention is derived from the same species as the patient being treated. For example, for treating a human, a human TNFα mutein can be used as the binding partner, which is expected to have low immunogenicity given the homology to the endogenous TNFα. Similarly, muteins derived from other mammalian species can be used in the respective species.

As disclosed herein, TNFα muteins are particularly useful binding partners in methods of the invention. A number of TNFα muteins have been previously described (see, for example, Van Ostade et al., *Protein Eng.* 7:5-22 (1994); Van Ostade et al., *EBMO J.* 10:827-836 (1991); Zhang et al., *J. Biol. Chem.* 267:24069-24075 (1992); Yamagishi et al., *Protein Eng.* 3:713-719 (1990), each of which is incorporated herein by reference). Specific exemplary muteins include the human TNFα muteins shown in FIG. 3B.

There are several advantages to using TNFα muteins as binding partners in the present invention. Although TNFα muteins can display lower binding activity for TNF receptors, some TNFα muteins bind only 5- to 17-fold less effectively than native TNFα. Such a binding affinity, albeit reduced relative to native TNFα, can still be an effective binding partner in the present invention (see Example 3). Another advantage of using TNFα muteins is that some exhibit decreased signaling through membrane receptors, for example, decreased cytotoxic activity or in vivo toxicity, relative to native TNFα. In particular, muteins 1, 2, 3, 4, 5 and 6 exhibit a 200- to 10,000-fold decrease in cytotoxicity (see below and Van Ostade, supra, 1994; Yamagishi et al., supra, 1990; Zhang et al., supra, 1992). Thus, even though the binding affinity is reduced 10- to 17-fold, there can be a 200- to 10,000-fold decrease in signaling through membrane receptors, for example, decreased cytotoxic activity or in vivo toxicity. As discussed above, such a reduced signaling through membrane receptors, for example, reduced cytotoxicity or in vivo toxicity, is advantageous in view of the potential leaching of the ligand from a matrix and introduction of low levels into a patient when an altered biological fluid is returned to the patient.

An additional advantage of using TNFα muteins is that they have a native structure. Because the muteins are highly homologous to the native TNFα sequence, these muteins can fold into a native structure that retains TNF receptor binding activity. Such a native structure means that the same amino acid residues are exposed on the surface of the molecule as in the native TNFα, except for possibly the mutant amino acid residue. Such a native folding means that the TNFα muteins should have little or no immunogenicity in the respective mammalian species.

As disclosed herein, particularly useful muteins are human muteins 1, 2, 3, 4, 5 and 6 (FIG. 3B) and the analogous muteins in other mammalian species. Mutein 1 is a single amino acid substitution relative to wild type human TNFα of $Arg^{31}$ with Pro (Zhang et al., supra, 1992). This mutein exhibits approximately 10-fold lower binding activity and approximately 10,000-fold lower cytotoxicity relative to native TNFα. Mutein 2 is a single amino acid substitution relative to wild type human TNFα of $Asn^{34}$ with Tyr (Yamagishi et al., supra, 1990; $Asn^{32}$ in the numbering system of Yamagishi et al.). This mutein exhibits approximately 5-fold lower binding activity and approximately 12,500-fold lower cytotoxicity relative to native TNFα. Mutein 3 is a single amino acid substitution relative to wild type human TNFα of $Pro^{117}$ with Leu (Yamagishi et al., supra, 1990; Pro 115 in the numbering system of Yamagishi et al.). This mutein exhibits approximately 12-fold lower binding activity and approximately 1400-fold lower cytotoxicity. Mutein 4 is a single amino acid substitution relative to wild type human TNFα of $Ser^{147}$ with Tyr (Zhang et al., supra, 1992). This mutein exhibits approximately 14-fold lower binding activity and approximately 10,000-fold lower cytotoxicity relative to native TNFα. Mutein 5 is a single amino acid substitution relative to wild type human TNFα of $Ser^{95}$ with Tyr (Zhang et al., supra, 1992). This mutein exhibits approximately 17-fold lower binding activity and approximately 200-fold lower cytotoxicity relative to native TNFα. Mutein 6 is a single amino acid substitution relative to wild type human TNFα of $Tyr^{115}$ with Phe (Zhang et al., supra, 1992). This mutein exhibits approximately 17-fold lower binding activity and approximately 3,300-fold lower cytotoxicity relative to native TNFα. As disclosed herein, it is understood that analogous muteins can be generated in other mammalian species by making the same amino acid substitutions in the analogous position of the respective species.

Although muteins 1, 2 and 4, as well as other TNFα muteins, were previously known and characterized with respect to binding the multivalent membrane receptor, it was previously unknown whether these TNFα muteins would bind to the monovalent soluble TNF receptors. As disclosed herein, the TNFα muteins bind with an affinity sufficient to deplete soluble TNF receptor from plasma (see Example 3). These results indicate that TNFα muteins can be an effective binding partner for depleting soluble TNF receptor from a biological fluid.

It is understood that TNFα muteins additional to the specific muteins exemplified herein can be used in methods of the invention. TNFα from various mammalian species show a high degree of amino acid identity (see FIGS. 3A and 3B, conserved sequence SEQ ID NO:1; Van Ostade et al., supra, 1994). As described by Van Ostade et al. (supra, 1994), a conserved TNFα amino acid sequence was identified across 11 mammalian species. The conserved amino acid residues are conserved across all 11 shown species or have only a single species showing variation at that position (see FIG. 3A and Van Ostade et al., supra, 1994). Thus, in one embodiment, the invention provides a TNFα mutein comprising the conserved sequence referenced as SEQ ID NO:1.

One skilled in the art can readily determine additional muteins suitable for use in methods of the invention. As discussed above, TNFα muteins having relatively high affinity for TNF receptors and decreased signaling through membrane receptors, for example, decreased cytotoxicity or in vivo toxicity, relative to native TNFα are particularly useful in methods of the invention. One skilled in the art can readily determine additional suitable TNFα muteins based on methods well known to those skilled in the art. Methods for introducing amino acid substitutions into a sequence are well known to those skilled in the art (Ausubel et al., *Current Protocols in Molecular Biology* (Supplement 56), John Wiley & Sons, New York (2001); Sambrook and Russel, *Molecular Cloning: A Laboratory Manual,* 3rd ed., Cold Spring Harbor Press, Cold Spring Harbor (2001); U.S. Pat. Nos. 5,264,563 and 5,523,388). Generation of TNFα muteins has been previously described (Van Ostade et al., supra, 1994; Van Ostade et al., supra, 1991; Zhang et al., supra, 1992; Yamagishi et al., supra, 1990). Furthermore, one skilled in the art can readily determine the binding and cytotoxicity and/or in vivo toxicity of candidate muteins to ascertain the suitability for use in a method of the invention (Van Ostade et al., supra, 1994; Van Ostade et al., supra, 1991; Zhang et al., supra, 1992; Yamagishi et al., supra, 1990).

Muteins of particular interest for use in methods of the present invention, in addition to having relatively high affinity for TNF receptors and reduced signaling through membrance receptors, for example, reduced cytotoxicity or in vivo toxicity, are those having amino acid substitutions in three regions of TNFα, region 1, amino acids 29-36, region 2, amino acids 84-91, and region 3, amino acids 143-149 (numbering as shown in FIG. 3A). Muteins 1, 2 and 4 are exemplary of muteins having single amino acid substitutions in these regions. Region 1 corresponds to amino acids 29-36, residues LNRRANAL (SEQ ID NO:18) of human TNFα. Region 2 corresponds to amino acids 84-91, residues AVSYQTKV (SEQ ID NO:19) of human TNFα. Region 3 corresponds to amino acids 143-149, residues DFAESG (SEQ ID NO:20) of human TNFα. In addition to the TNFα muteins disclosed herein, other TNFα muteins can be generated, for example, by introducing single amino acid substitutions in regions 1, 2 or 3 and screening for binding activity and cytotoxic activity and/or in vivo toxicity as disclosed herein (see also Van Ostade et al., supra, 1991; Zhang et al, supra, 1992; Yamagishi et al., supra, 1990). Methods for introducing amino acid substitutions at a particular amino acid residue or region are well known to those skilled in the art (see, for example, Van Ostade et al., supra, 1991; Zhang et al, supra, 1992; Yamagishi et al., supra, 1990; U.S. Pat. Nos. 5,264,563 and 5,523,388). For example, each of the other 19 amino acids relative to a native sequence can be introduced at each of the positions in regions 1, 2 and 3 and screened for binding activity and/or signaling activity, for example, cytotoxic activity or in vivo toxicity, to soluble and/or membrane bound TNF receptor. This would only require the generation of approximately 420 mutants (19 single amino acid substitutions at each of 22 positions in regions 1, 2 and 3), a number which can be readily generated and screened by well known methods. Those having desired characteristics as disclosed herein, for example, specific binding activity for soluble TNF receptor and reduced signaling through the membrane TNF receptor, can be selected as a TNFα mutein useful in methods of the invention.

The invention additionally provides a TNFα mutein having the consensus sequence of SEQ ID NO:9 (FIG. 3C). In one embodiment, a TNFα mutein comprises the consensus sequence SEQ ID NO:9, wherein $X_1$ is an amino acid selected from Leu and Val; wherein $X_2$ is a 2 or 3 amino acid peptide selected from GlnAsnSer, ArgAlaLeu, ArgThrPro, GlnAlaSer, and GlnThr; wherein $X_3$ is an amino acid selected from Asp and Asn; wherein $X_4$ is a 5 amino acid peptide selected from HisGlnValGluGlu, HisGlnAlaGluGlu, ProGlnValGluGly, ProGluAlaGluGly, LeuSerAlaProGly, IleSerAlaProGly, ProGlnAlaGluGly, IleAsnSerProGly, and ValLysAlaGluGly; wherein $X_5$ is an amino acid selected from Glu, Gln and Arg; wherein $X_6$ is a 4 amino acid peptide selected from LeuSerGlnArg, LeuSerArgArg, GlyAspSerTyr, LeuSerGlyArg, TrpAspSerTyr, GinSerGlyTyr, and LeuAsnArgArg; wherein $X_7$ is an amino acid selected from Leu, Met, and Lys; wherein $X_8$ is a two amino acid peptide selected from MetAsp, MetLys, ValGlu, ValLys, and ValGln; wherein $X_9$ is an amino acid selected from Lys, Thr, Glu, and Arg; wherein $X_{10}$ is an amino acid selected from Val, Lys, and Ile; wherein $X_{11}$ is a 2 amino acid peptide selected from AlaAsp, SerAsp, ThrAsp, LeuAsp, AlaGlu, and SerGlu; wherein $X_{12}$ is an amino acid selected from Lys, Ser, Thr, and Arg; wherein $X_{13}$ is an amino acid selected from Gln and His; wherein $X_{14}$ is a 4 or 5 amino acid peptide selected from AspValValLeu, AspTyrValLeu, SerTyrValLeu, ProProProVal, SerThrHisValLeu, SerThrProLeuPhe, SerThrHisValLeu, and SerThrAsnValPhe; wherein $X_{15}$ is an amino acid selected from Val and Ile; wherein $X_{16}$ is an amino acid selected from Phe, Ile, and Leu; wherein $X_{17}$ is an amino acid selected from Ile and Val; wherein $X_{18}$ is a 2 amino acid peptide selected from GlnGlu, ProAsn, GlnThr, and ProSer; wherein $X_{19}$ is an amino acid selected from Leu and Ile; wherein $X_{20}$ is a 3 amino acid peptide selected from ProLysAsp, HisArgGlu, GlnArgGlu, and HisThrGlu; wherein $X_{21}$ is an amino acid selected from Gly, Glu, Gln, and Trp or is absent; wherein $X_{22}$ is an amino acid selected from Leu, Pro, and Ala; wherein $X_{23}$ is an amino acid selected from Leu and Gln; wherein $X_{24}$ is an amino acid selected from Gly and Asp; wherein $X_{25}$ is an amino acid selected from Gln, Leu, and Arg; wherein $X_{26}$ is an amino acid selected from Ala and Thr; wherein $X_{27}$ is an amino acid selected from Val and Ile; wherein $X_{28}$ is an amino acid selected from Leu, Gin, and Arg; wherein $X_{29}$ is an amino acid selected from Lys, Glu, Ala, Asn, and Asp; wherein $X_{30}$ is an amino acid selected from Phe, Ile, Leu and Tyr; and wherein $X_{31}$ is an amino acid selected from Val and Ile (see FIG. 3A; Van Ostade et al., supra, 1994). Such a consensus TNFα mutein is expected to exhibit binding activity for TNF receptor, and such activity can be readily determined by those skilled in the art using well known methods, as disclosed herein.

In addition to the variant positions described above, it is understood that a TNFα mutein can additionally include variant amino acids in the conserved sequence referenced as SEQ ID NO:1. As shown in FIG. 3A and as discussed above, the conserved TNFα sequence includes certain positions where one of the shown mammalian species differs from the other ten. For example, the conserved amino acid at position 2, Arg, is Leu in dog (FIG. 3A). Thus, a TNFα mutein can include a substitution of Leu at position 2 with the remainder of the conserved sequence referenced as SEQ ID NO:1. Similarly, substitutions of other "conserved" positions, where at least one of the species has an amino acid substitution relative to the conserved sequence, are included as TNFα muteins. For example, a TNFα mutein can have the corresponding substitution of mutein 1, that is, $Arg^{31}Pro$ and substitution in the conserved sequence in the variable positions, as described above represented by X, and/or substitution in a conserved position that varies in a single species. Furthermore, a TNFα mutein can include conservative amino acid substitutions relative to the conserved sequence or the sequence of a particular species of TNFα. Such TNFα muteins can be readily recognized by one skilled in the art based on the desired characteristics of a TNFα mutein, as disclosed herein.

Additionally, any of the TNFα muteins disclosed herein can be modified to include an N-terminal deletion. As discussed in Van Ostade (supra, 1994), short deletions at the N-terminus of TNFα retained activity, whereas deletion of the N-terminal 17 amino acids resulted in a loss of activity. Therefore, it is understood that a TNFα mutein of the invention also includes TNFα muteins having N-terminal deletions that retain activity. Such TNFα muteins can include, for example, an N-terminal deletion of 1, 2, 3, 4, 5, 6, 7, 8, 9 or 10 amino acids. Furthermore, one skilled in the art can readily determine whether further N-terminal deletions can be incorporated into a TNFα mutein by making the deletion mutations and screening for desired characteristics, as disclosed herein.

The invention provides a variety of TNFα muteins, as disclosed herein. Generally, a particularly useful TNFα mutein of the invention has about 2-fold, about 3-fold, about 4-fold, about 5-fold, about 6-fold, about 7-fold, about 8-fold, about 9-fold, about 10-fold, about 11-fold, about 12-fold, about 13-fold, about 14-fold, about 15-fold, about 16-fold, about 17-fold, about 18-fold, about 19-fold, about 20-fold, about 25-fold, about 30-fold, or even higher fold reduced binding affinity for TNF receptors, particularly membrane bound TNF receptors, relative to native/wild type TNFα. Such reduced binding affinity can be, but is not necessarily, exhibited toward sTNFR. Also, a particularly useful TNFα mutein of the invention has about 10-fold, about 50-fold, about 100-fold, about 150-fold, about 200-fold, about 300-fold, about 500-fold, about 1000-fold, about 2000-fold, about 3000-fold, about 4000-fold, about 5000-fold, about 6000-fold, about 7000-fold, about 8000-fold, about 9000-fold, about 10,000-fold, about 20,000-fold, about 30,000-fold, about 50,000-fold, or even higher fold reduced signaling through the membrane receptors, for example, reduced cytoxicity or in vivo toxicity, relative to native/wild type TNFα. It is understood that a TNFα mutein can have reduced binding affinity and/or reduced cytoxicity, as discussed above and disclosed herein.

The invention provides a conjugate comprising a tumor necrosis factor α (TNFα) mutein attached to a substrate. In one embodiment, the TNFα mutein of the conjugate comprises the conserved sequence referenced as SEQ ID NO:1.

In another embodiment, the invention provides a conjugate where the TNFα mutein has the consensus sequence SEQ ID NO:9, wherein $X_1$ is an amino acid selected from Leu and Val; wherein $X_2$ is a 2 or 3 amino acid peptide selected from GlnAsnSer, ArgAlaLeu, ArgThrPro, GlnAlaSer, and GlnThr; wherein $X_3$ is an amino acid selected from Asp and Asn; wherein $X_4$ is a 5 amino acid peptide selected from HisGlnValGluGlu, HisGlnAlaGluGlu, ProGInValGluGly, ProGluAlaGluGly, LeuSerAlaProGly, IleSerAlaProGly, ProGlnAlaGluGly, IleAsnSerProGly, and ValLysAlaGluGly; wherein $X_5$ is an amino acid selected from Glu, Gln and Arg; wherein $X_6$ is a 4 amino acid peptide selected from LeuSerGlnArg, LeuSerArgArg, GlyAspSerTyr, LeuSerGlyArg, TrpAspSerTyr, GlnSerGlyTyr, and LeuAsnArgArg; wherein $X_7$ is an amino acid selected from Leu, Met, and Lys; wherein $X_8$ is a two amino acid peptide selected from MetAsp, MetLys, ValGlu, ValLys, and ValGln; wherein $X_9$ is an amino acid selected from Lys, Thr, Glu, and Arg; wherein $X_{10}$ is an amino acid selected from Val, Lys, and Ile; wherein $X_{11}$ is a 2 amino acid peptide selected from AlaAsp, SerAsp, ThrAsp, LeuAsp, AlaGlu, and SerGlu; wherein $X_{12}$ is an amino acid selected from Lys, Ser, Thr, and Arg; wherein $X_{13}$ is an amino acid selected from Gln and His; wherein $X_{14}$ is a 4 or 5 amino acid peptide selected from AspValValLeu, AspTyrValLeu, SerTyrValLeu, ProProProVal, SerThrHisValLeu, SerThrProLeuPhe, SerThrHisValLeu, and SerThrAsnValPhe; wherein $X_{15}$ is an amino acid selected from Val and Ile; wherein $X_{16}$ is an amino acid selected from Phe, Ile, and Leu; wherein $X_{17}$ is an amino acid selected from Ile and Val; wherein $X_{18}$ is a 2 amino acid peptide selected from GlnGlu, ProAsn, GlnThr, and ProSer; wherein $X_{19}$ is an amino acid selected from Leu and Ile; wherein $X_{20}$ is a 3 amino acid peptide selected from ProLysAsp, HisArgGlu, GlnArgGlu, and HisThrGlu; wherein $X_{21}$ is an amino acid selected from Gly, Glu, Gln, and Trp or is absent; wherein $X_{22}$ is an amino acid selected from Leu, Pro, and Ala; wherein $X_{23}$ is an amino acid selected from Leu and Gln; wherein $X_{24}$ is an amino acid selected from Gly and Asp; wherein $X_{25}$ is an amino acid selected from Gln, Leu, and Arg; wherein $X_{26}$ is an amino acid selected from Ala and Thr; wherein $X_{27}$ is an amino acid selected from Val and Ile; wherein $X_{28}$ is an amino acid selected from Leu, Gln, and Arg; wherein $X_{29}$ is an amino acid selected from Lys, Glu, Ala, Asn, and Asp; wherein $X_{30}$ is an amino acid selected from Phe, Ile, Leu and Tyr; and wherein $X_{31}$ is an amino acid selected from Val and Ile.

In yet another embodiment, the invention provides a conjugate where the TNFα mutein has an amino acid substitution in a region of TNFα selected from region 1 amino acids 29-36, region 2 amino acids 84-91 and region 3 amino acids 143-149 of human TNFα (SEQ ID NO:2) or the analogous position of TNFα from another species.

In still another embodiment, the invention provides a conjugate where the TNFα mutein is selected from mutein 1 (SEQ ID NO:3), mutein 2 (SEQ ID NO:4), mutein 3 (SEQ ID NO:5), mutein 4 (SEQ ID NO:6), mutein 5 (SEQ ID NO:7) and mutein 6 (SEQ ID NO:8). In a particular embodiment, the invention provides a conjugate where the TNFα mutein is selected from mutein 1 (SEQ ID NO:3), mutein 2 (SEQ ID NO:4), and mutein 4 (SEQ ID NO:6). The TNFα mutein of the conjugate can be derived from a species selected, for example, from human, dog, cat, horse, sheep, goat, pig, cow, rabbit and rat.

The invention additionally provides a method of stimulating an immune response in a mammal having a pathological condition. The method can include the steps of obtaining a biological fluid from the mammal; contacting the biological fluid with a tumor necrosis factor α (TNFα) mutein having specific binding activity for a soluble tumor necrosis factor receptor (TNFR); removing the TNFα mutein bound to the soluble TNFR from the biological fluid to produce an altered biological fluid having a reduced amount of soluble TNFR; and administering the altered biological fluid to the mammal. The biological fluid can be, for example, blood, plasma, serum or lymphatic fluid, including whole blood. In one embodiment, a method using whole blood as the biological fluid can further include the step of separating the whole blood into a cellular component and an acellular component or a fraction of the acellular component, wherein the acellular or the fraction of the acellular component contains a soluble TNFR. The method can additionally include the step of combining the cellular component with the altered acellular component or altered fraction of the acellular component to produce altered whole blood, which is administered to the mammal as the altered biological fluid.

In a particular embodiment of a method of the invention, the TNFα mutein can have specific binding activity for a single type of soluble TNFR, for example sTNFRI or sTNFRII. Alternatively, the TNFα mutein can have specific binding activity for more than one type of soluble TNFR, for example, both sTNFRI and sTNFRII.

The present invention further relates to the use of various mixtures of binding partners. One mixture can be composed of multiple binding partners that selectively bind to a single targeted immune system inhibitor. Another mixture can be composed of multiple binding partners, each of which selectively binds to different targeted immune system inhibitors. Alternatively, the mixture can be composed of multiple binding partners that selectively bind to different targeted immune system inhibitors. For example, the mixture can contain more than one TNFα mutein. Furthermore, the multiple TNFα muteins can specifically bind to a single type of soluble TNF receptor or can bind to more than one type of TNF receptor, for example, sTNFRI and sTNFRII.

In another embodiment of a method of the invention, the biological fluid can be contacted with a plurality of TNFα muteins. In a particular embodiment, the plurality of TNFα muteins can have specific binding activity for a single type of soluble TNFR, for example, sTNFRI or sTNFRII. Alternatively, the plurality of TNFα muteins can have specific binding activity for more than one type of soluble TNFR, that is, sTNFRI and sTNFRII.

For certain embodiments in which it is desirable to increase the molecular weight of the binding partner/immune system inhibitor complex, the binding partner can be conjugated to a carrier. Examples of such carriers include, but are not limited to, proteins, complex carbohydrates, and synthetic polymers such as polyethylene glycol.

As used herein, "functionally active binding sites" of a binding partner refer to sites that are capable of binding to one or more targeted immune system inhibitors.

Methods for producing the various binding partners useful in the present invention are well known to those skilled in the art. Such methods include, for example, recombinant DNA and synthetic techniques, or a combination thereof. Binding partners such as TNFα muteins can be expressed in prokaryotic or eukaroytic cells, for example, mammalian, insect, yeast, and the like. If desired, codons can be changed to reflect any codon bias in a host species used for expression.

In one embodiment of the present methods, the binding partner such as a TNFα mutein is attached to an inert medium to form an absorbent matrix (FIG. 1). The TNFα mutein can be, for example, covalently attached to a substrate such as an inert medium. As used herein, the term "inert medium" is intended to include solid supports to which the binding partner(s) can be attached. Particularly useful supports are materials that are used for such purposes including, for example, cellulose-based hollow fibers, synthetic hollow fibers, silica-based particles, flat or pleated membranes, macroporous beads, agarose-based particles, and the like. The inert medium can be in the form of a bead, for example, a macroporous bead or a non-porous bead. Exemplary macroporous beads include, but are not limited to, naturally occurring materials such as agarose, cellulose, controlled pore glass, or synthetic materials such as polyacrylamide, cross-linked agarose (such as Trisacryl™, Sephacryl, and Ultrogel™), azlactone, polymethacrylate, polystyrene/divinylbenzene, and the like. Exemplary non-porous beads include, but are not limited to, silica, polystyrene, latex, and the like. Hollow fibers and membranes can also be composed of natural or synthetic materials. Exemplary natural materials include, but are not limited to, cellulose and modified cellulose, for example, cellulose diacetate or triacetate. Exemplary synthetic materials include, but are not limited to, polysulfone, polyvinyl, polyacetate, and the like. Such inert media can be obtained commercially or can be readily made by those skilled in the art. The binding partner can be attached to the inert medium by any means known to those skilled in the art including, for example, covalent conjugation. Alternatively, the binding partner can be associated with the inert matrix through high-affinity, non-covalent interaction with an additional molecule which has been covalently attached to the inert medium. For example, a biotinylated binding partner can interact with avidin or streptavidin previously conjugated to the inert medium.

The absorbent matrix thus produced can be contacted with a biological fluid, or a fraction thereof, through the use of an extracorporeal circuit. The development and use of extracorporeal, absorbent matrices has been extensively reviewed (see Kessler, *Blood Purification* 11:150-157 (1993)).

Figure 2:
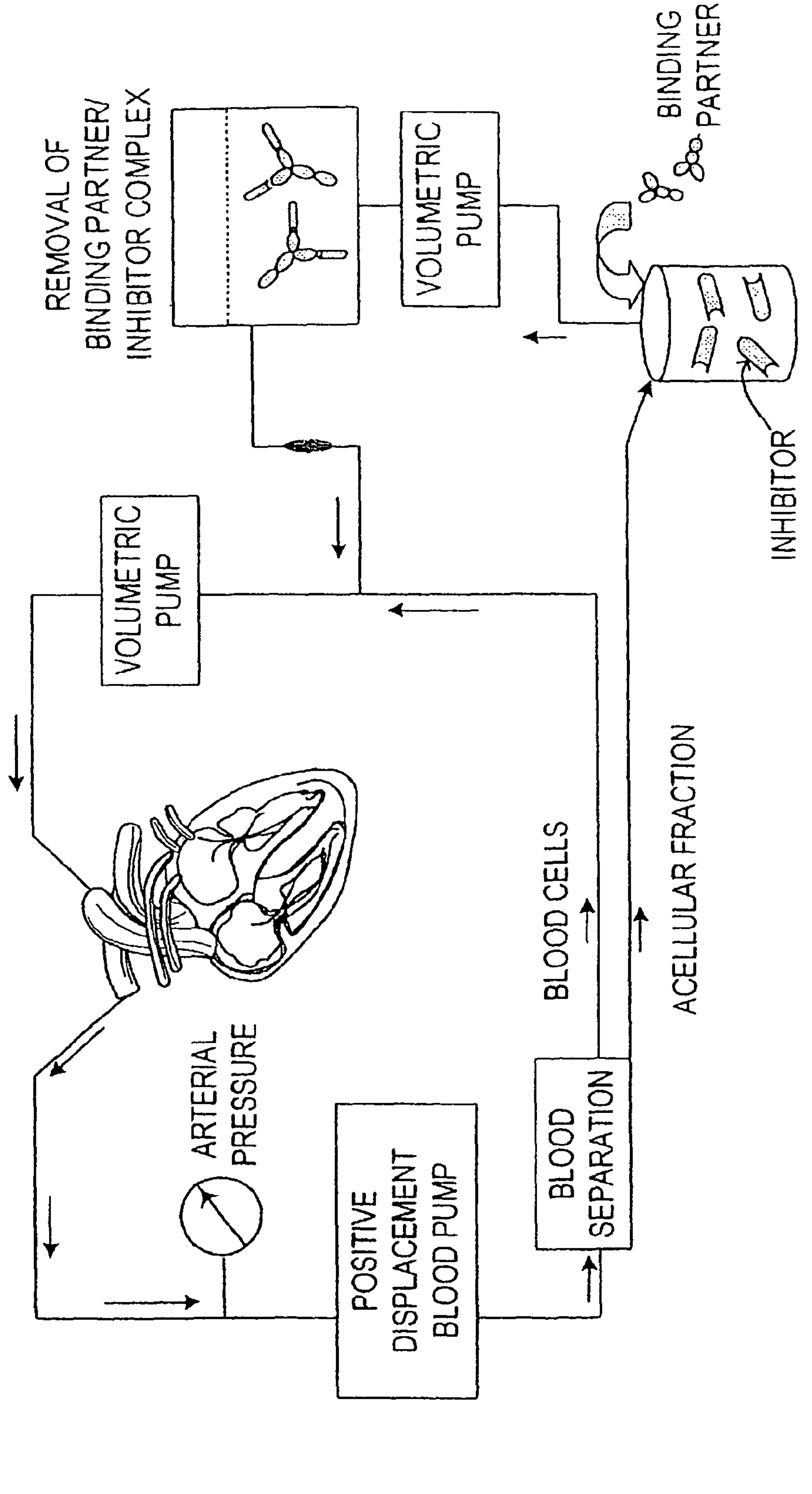
FIG. 2 schematically illustrates a "stirred reactor" configuration of an embodiment of the invention. In this example, blood is removed from the patient and separated into a cellular and an acellular component, or fractions thereof. A binding partner such as a TNFα mutein is added to the acellular component, or fractions thereof. Subsequently, the binding partner (TNFα mutein)/immune system inhibitor (soluble TNF receptor) complex is removed by mechanical or by chemical or biological means from the acellular component, or fractions thereof, and the altered biological fluid is returned contemporaneously to the patient.

In another embodiment, herein referred to as the "stirred reactor" (FIG. 2), the biological fluid is exposed to the binding partner such as a TNFα mutein in a mixing chamber and, thereafter, the binding partner/immune system inhibitor complex is removed by means known to those skilled in the art, including, for example, by mechanical or by chemical or biological separation methods. For example, a mechanical separation method can be used in cases where the binding partner, and therefore the binding partner/immune system inhibitor complex, represent the largest components of the treated biological fluid. In those cases, filtration can be used to retain the binding partner and immune system inhibitors associated therewith, while allowing all other components of the biological fluid to permeate through the fiber and, thus, to be returned to the patient. In an example of a chemical or biological separation method, the binding partner and immune system inhibitors associated therewith can be removed from the treated biological fluid through exposure to an absorbent matrix capable of specifically attaching to the binding partner. For example, a matrix constructed with antibodies reactive with a TNFα mutein can serve this purpose. Similarly, were biotin conjugated to the binding partner such as a TNFα mutein prior to its addition to the biological fluid, a matrix constructed with avidin or streptavidin could be used to deplete the binding partner and immune system inhibitors associated therewith from the treated fluid.

In a final step of the present methods, the treated or altered biological fluid, having a reduced amount of targeted immune system inhibitor such as soluble TNF receptor, is returned to the patient receiving treatment along with untreated fractions of the biological fluid, if any such fractions were produced during the treatment. The altered biological fluid can be administered to the mammal by any means known to those skilled in the art, including, for example, by infusion directly into the circulatory system. The altered biological fluid can be administered immediately after contact with the binding partner in a contemporaneous, extracorporeal circuit. In this circuit, the biological fluid is (a) collected, (b) separated into cellular and acellular components, if desired, (c) exposed to the binding partner, and if needed, separated from the binding partner bound to the targeted immune system inhibitor, (d) combined with the cellular component, if needed, and (e) readministered to the patient as altered biological fluid. Alternatively, the administration of the altered biological fluid can be delayed under appropriate storage conditions readily determined by those skilled in the art.

If desirable, the entire process can be repeated. Those skilled in the art can readily determine the benefits of repeated treatment by monitoring the clinical status of the patient, and correlating that status with the concentration(s) of the targeted immune system inhibitor(s) such as soluble TNFα receptor in circulation prior to, during, and after treatment.

The present invention further provides an apparatus for reducing the amount of a targeted immune system inhibitor such as soluble TNF receptor in a biological fluid. The apparatus is composed of: (a) a means for separating the biological fluid into a cellular component and an acellular component or fraction thereof; (b) an absorbent matrix having attached thereto a TNFα mutein or a stirred reactor as described above to produce an altered acellular component or fraction thereof; and (c) a means for combining the cellular fraction with the altered acellular component or fraction thereof. The apparatus is particularly useful for whole blood as the biological fluid in which the cellular component is separated either from whole plasma or a fraction thereof.

The means for initially fractionating the biological fluid into the cellular component and the acellular component, or a fraction thereof, and for recombining the cellular component with the acellular component, or fraction thereof, after treatment are known to those skilled in the art (see *Apheresis: Principles and Practice*, supra).

In a specific embodiment, the immune system inhibitor to be targeted is sTNFRI (Seckinger et al., *J. Biol. Chem.* 264: 11966-11973 (1989); Gatanaga et al., *Proc. Natl. Acad. Sci. USA* 87:8781-8784 (1990)), a naturally occurring inhibitor of the pluripotent immune system stimulator, TNF. sTNFRI is produced by proteolytic cleavage, which liberates the extracellular domain of the membrane tumor necrosis factor receptor type I from its transmembrane and intracellular domains (Schall et al., *Cell* 61:361-370 (1990); Himmler et al., *DNA and Cell Biol.* 9:705-715 (1990)). sTNFRI retains the ability to bind to TNF with high affinity and, thus, to inhibit the binding of TNF to the membrane receptor on cell surfaces.

The levels of sTNFRI in biological fluids are increased in a variety of conditions which are characterized by an antecedent increase in TNF. These include bacterial, viral, and parasitic infections, and cancer as described above. In each of these disease states, the presence of the offending agent stimulates TNF production which stimulates a corresponding increase in sTNFRI production. sTNFRI production is intended to reduce localized, as well as systemic, toxicity associated with elevated TNF levels and to restore immunologic homeostasis.

In tumor bearing hosts, over-production of sTNFRI may profoundly affect the course of disease, considering the critical role of TNF in a variety of anti-tumor immune responses (reviewed in, Beutler and Cerami, *Ann. Rev. Immunol.* 7:625-655 (1989)). TNF directly induces tumor cell death by binding to the type I membrane-associated TNF receptor. Moreover, the death of vascular endothelial cells is induced by TNF binding, destroying the circulatory network serving the tumor and further contributing to tumor cell death. Critical roles for TNF in natural killer cell- and cytotoxic T lymphocyte-mediated cytolysis also have been documented. Inhibition of any or all of these effector mechanisms by sTNFRI has the potential to dramatically enhance tumor survival.

That sTNFRI promotes tumor survival, and that its removal enhances anti-tumor immunity, has been demonstrated. In an experimental mouse tumor model, sTNFRI production was found to protect transformed cells in vitro from the cytotoxic effects of TNF, and from cytolysis mediated by natural killer cells and cytotoxic T lymphocytes (Selinsky et al., *Immunol.* 94:88-93 (1998)). In addition, the secretion of sTNFRI by transformed cells has been shown to markedly enhance their tumorigenicity and persistence in vivo (Selinsky and Howell, *Cell. Immunol.* 200:81-87 (2000)). Moreover, removal of circulating sTNFRI has been found to provide clinical benefit to cancer patients, as demonstrated by human trials of Ultrapheresis as discussed above (Lentz, supra). These observations affirm the importance of this molecule in tumor survival and suggest the development of methods for more specific removal of sTNFRI as promising new avenues for cancer immunotherapy.

The following examples are intended to illustrate but not limit the invention.

Example 1

Production, Purification, and Characterization of the Immune System Inhibitor, Human sTNFRI The sTNFRI used in the present studies was produced recombinantly either in *E. coli* (R&D Systems; Minneapolis Minn.) or in eukaryotic cell culture essentially as described (see U.S. Pat. No. 6,379,708, which is incorporated herein by reference). The construction of the eukaryotic expression plasmid, the methods for transforming and selecting cultured cells, and for assaying the production of sTNFRI by the transformed cells have been described (Selinsky et al., supra, 1998).

sTNFRI was detected and quantified in the present studies by capture ELISA (Selinsky et al., supra). In addition, the biological activity of recombinant sTNFRI, that is, its ability to bind TNF, was confirmed by ELISA. Assay plates were coated with human TNFα (Chemicon; Temecula Calif.), blocked with bovine serum albumin, and sTNFRI, contained in culture supernatants as described above, was added. Bound sTNFRI was detected through the sequential addition of biotinylated-goat anti-human sTNFRI, alkaline phosphatase-conjugated streptavidin, and p-nitrophenylphosphate.

Example 2

Production, Purification, and Characterization of TNFα Muteins

Figure 4:
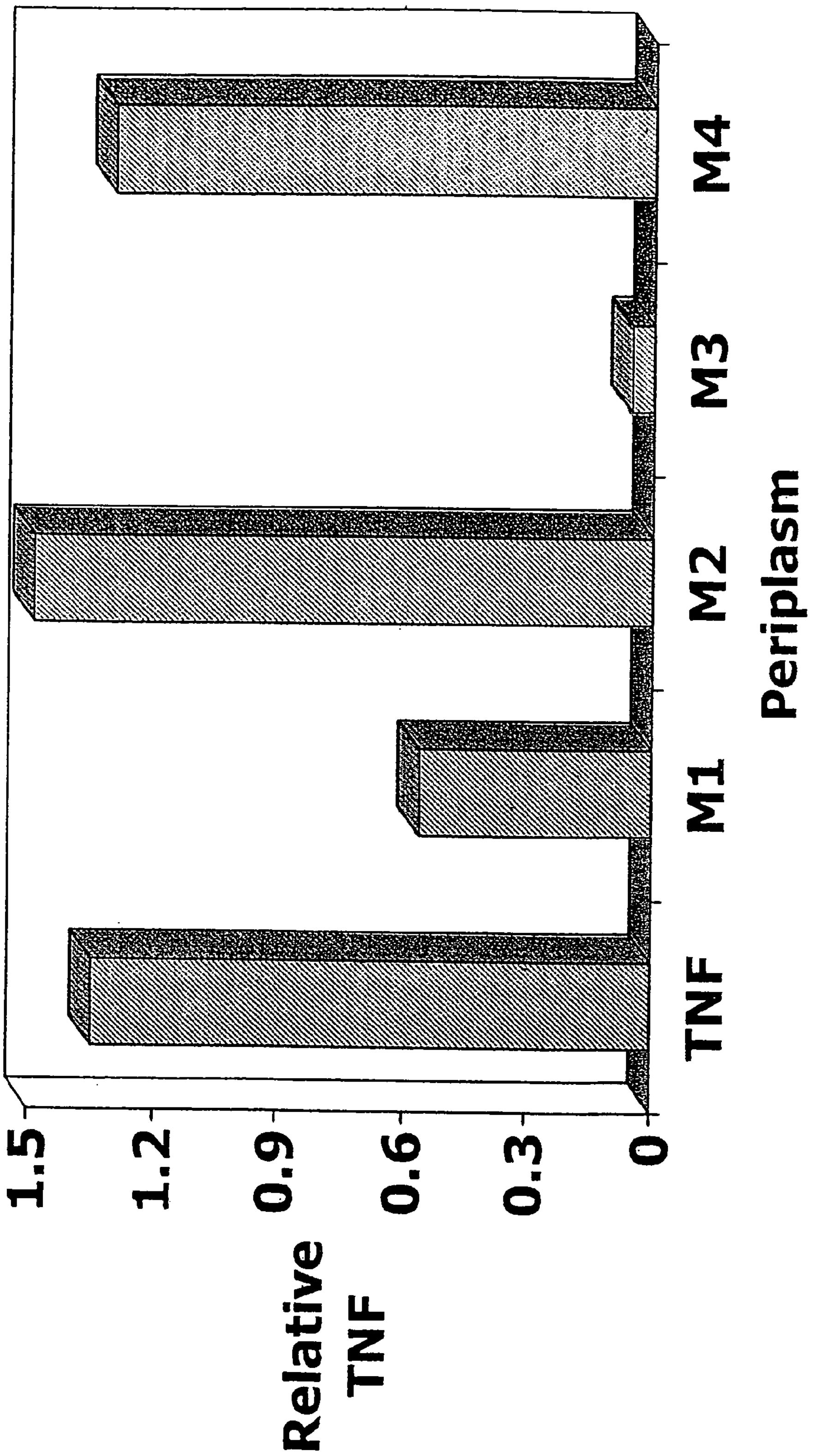
FIG. 4 shows the presence of human TNFα and TNFα muteins 1, 2, 3 and 4 in periplasmic preparations of *Escherichia coli* transformed with the respective expression constructs.

Briefly, TNFα muteins 1, 2, 3 and 4 were produced by expression of the respective cDNAs in *E. coli*. Genes encoding TNFα and TNFα muteins 1, 2, 3 and 4 were prepared using overlapping oligonucleotides having codons optimized for bacterial expression. Each of the coding sequences was fused in frame to that encoding the ompA leader to permit export of the recombinant polypeptides to the periplasm. Synthetic fragments were cloned into a pUC19 derivative immediately downstream of the lac Z promoter, and the resulting recombinant plasmids were introduced into *E. coli*. Recombinant bacteria were cultured to late-log, induced with isopropyl-β-D-thiogalactopyranoside (IPTG) for three hours, and harvested by centrifugation. Periplasmic fractions were prepared and tested by ELISA using polyclonal goat anti-human TNFα capture antibodies. After the addition of the diluted periplasms, bound TNFα and TNFα muteins 1, 2, 3 and 4 were detected by sequential addition of biotinylated polyclonal goat anti-human TNFα, streptavidin-alkaline phosphatase, and para-nitrophenyl phosphate (pNPP). TNFα and each of the TNFα muteins was detectable in the respective periplasms, though the level of TNFα mutein 3 only slightly exceeded the detection limit of the assay (FIG. 4).

The TNFα and TNFα mutein polypeptides 1, 2 and 4 were purified from periplasmic fractions by sequential chromatography on Q and S anion and cation exchange columns, respectively, essentially as described (Tavernier et al., *J. Mol. Biol.* 211:493-501 (1990)). The TNFα and TNFα mutein polypeptides were purified to >95% homogeneity as analyzed by sodium dodecyl sulfate polyacrylamide gel electrophoresis (SDS-PAGE). The gels revealed a 17 kDa band corresponding to TNFα or the muteins and a 34 kDa band, which was confirmed by Western blotting to be dimerized TNFα mutein.

Figure 5:
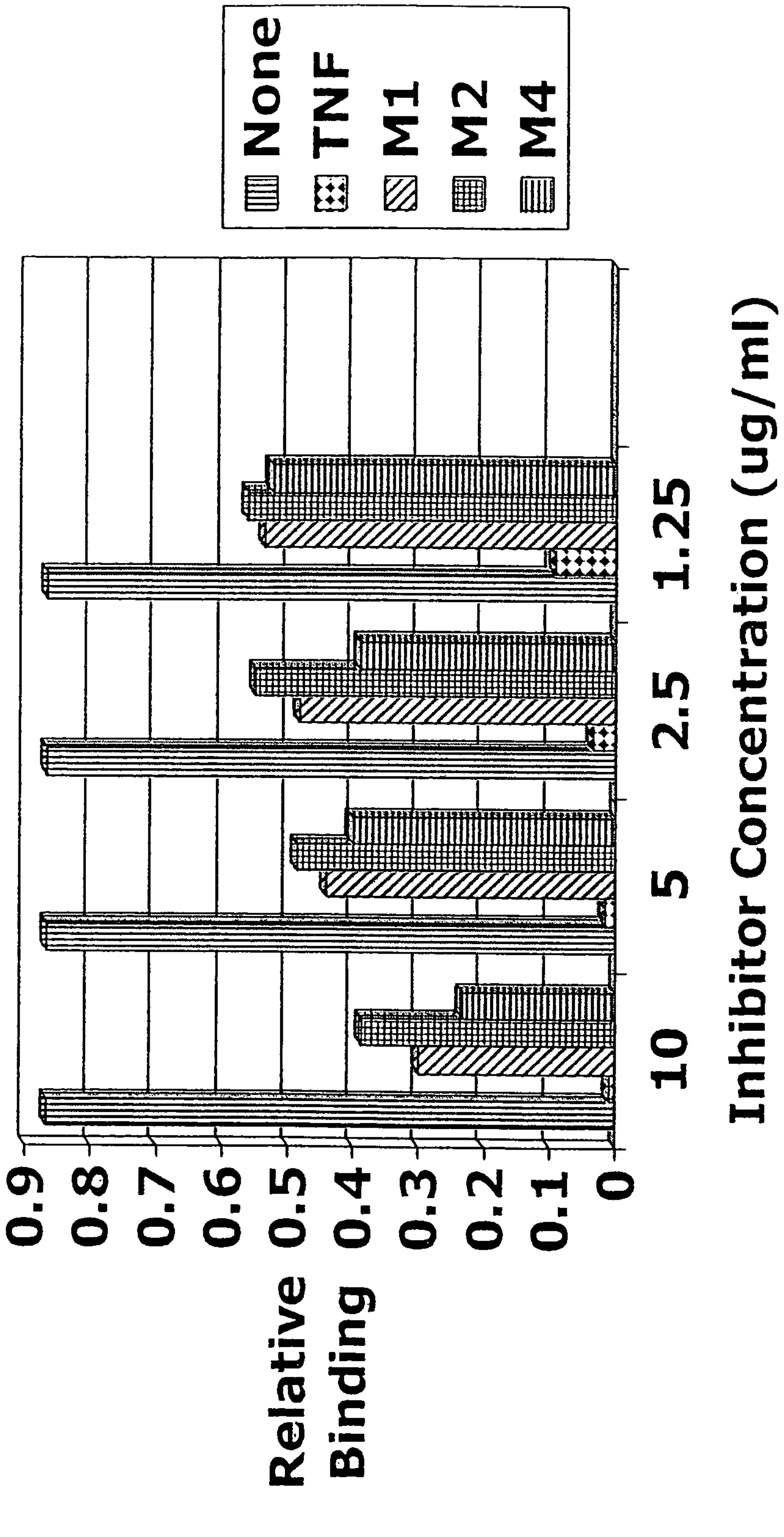
FIG. 5 shows that TNFα muteins bind to sTNFRI. Wells of a microtiter plate were coated with TNFα, blocked, and incubated with sTNFRI either in the presence or absence of the inhibitors, TNFα and TNFα muteins 1, 2 and 4.

The TNFα muteins were tested for their ability to bind to sTNFRI. Wells of a microtiter plate were coated with TNFα, blocked, and incubated with sTNFRI either in the presence or absence of the inhibitors, TNFα and TNFα muteins 1, 2 and 4. As shown in FIG. 5, TNFα muteins 1, 2 and 4 each bind to sTNFRI.

Example 3

Depletion of the Immune System Inhibitor, sTNFRI, From Human Plasma Using TNFα Mutein Absorbent Matrices The TNFα mutein absorbent matrices were produced and tested for their ability to deplete sTNFRI from human plasma. Briefly, purified TNFα muteins 1, 2 and 4 each was conjugated to cyanogen bromide (CNBr) Sepharose™ 4B at a density of 0.5 mg per ml of beads, and the remaining CNBr groups were quenched with ethanolamine. The resulting matrices were packed in individual column housings and washed extensively with phosphate buffered saline prior to use.

Normal human plasma was spiked (33% v/v) with culture supernatant containing recombinant human sTNFRI (see Example 1) to a final concentration of 8 nanograms per milliliter and passed through the respective columns at a flow rate of one milliliter of plasma per milliliter of resin per minute. An additional column, with no immobilized protein and quenched with ethanolamine, was included to control for non-specific depletion. One ml fractions were collected, and the relative levels of sTNFRI contained in the starting material and in the fractions were determined using a capture ELISA. To perform the capture ELISA, wells were coated with polyclonal goat anti-sTNFRI, and then were blocked with 2% BSA. Plasma samples were diluted 1:2, added to the wells, and sTNFRI therein was captured. Biotinylated polyclonal goat anti-sTNFRI was added, followed by streptavidin-alkaline phosphatase, and p-nitrophenylphosphate. Relative absorbance at 405 nm was used to estimate the depletion.

Figure 6:
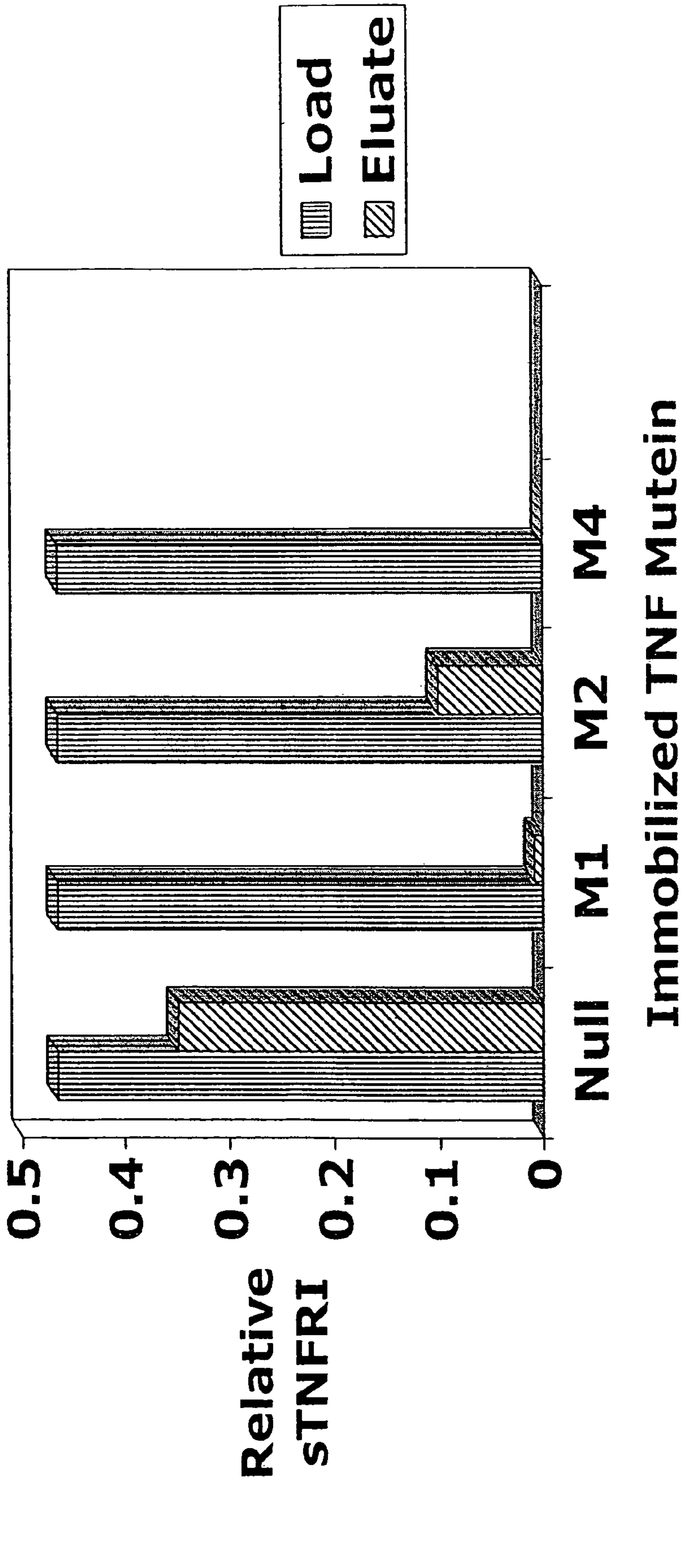
FIG. 6 shows the depletion of soluble TNF receptor I (sTNFRI) by immobilized TNF muteins. Muteins 1, 2 and 4 were immobilized on Sepharose™ 4B, and normal human plasma spiked with recombinant human sTNFRI was passed through columns of the immobilized muteins. Depletion of sTNFRI from the serum was measured by enzyme-linked immunosorbent assay (ELISA).

As shown in FIG. 6, all three of the immobilized TNFα muteins effectively depleted sTNFRI from human plasma, and the hierarchy observed in FIG. 5 again was manifested. The control matrix produced no reduction in sTNFRI levels, confirming the specificity of the depletion observed with the TNFα mutein matrices. Importantly, near quantitative depletion was achieved by TNFα muteins 1 and 4 at a flow rate that approximates that anticipated for use in a clinical setting.

Although the invention has been described with reference to the presently preferred embodiments, it should be understood that various modifications can be made without departing from the spirit of the invention. Accordingly, the invention is limited only by the following claims.

What is claimed is:

1. An absorbent matrix that facilitates the depletion of soluble TNF receptors from a mammalian biological fluid in an extracorporeal system, the absorbent matrix comprising:

a plurality of tumor necrosis factor-alpha (TNF-α) muteins comprising TNF-α mutein 4 (SEQ ID NO:6) immobilized on an extracorporeal biocompatible solid support, wherein the plurality of TNF-α muteins are covalently attached to the extracorporeal biocompatible solid support, and wherein the plurality of TNF-α muteins have a single amino acid substitution relative to an unsubstituted native TNF-α, and wherein each of the plurality of TNF-α muteins immobilized on the extracorporeal biocompatible solid support have a single binding site capable of selectively binding to one of the soluble TNF receptors with an affinity sufficient to deplete the soluble TNF receptors from the biological fluid.

2. The absorbent maxtrix of claim 1, wherein the plurality of TNF-α muteins further comprises mutein 1 (SEQ ID NO:3), mutein 2 (SEQ ID NO:4), mutein 3 (SEQ ID NO:5), mutein 5 (SEQ ID NO:7), mutein 6 (SEQ ID NO:8), or combinations thereof.

3. The absorbent maxtrix of claim 1, wherein the plurality of TNF-α muteins further comprises mutein 1 (SEQ ID NO:3), mutein 2 (SEQ ID NO:4), or combinations thereof.

4. The absorbent maxtrix of claim 1, wherein the biocompatible solid support is an inert medium.

5. The absorbent maxtrix of claim 1, wherein the biocompatible solid support is in the form of a bead.

6. The absorbent maxtrix of claim 5, wherein the bead is a macroporous bead.

7. The absorbent maxtrix of claim 6, wherein the macroporous bead is selected from agarose, cross-linked agarose, cellulose, controlled pore glass, polyacrylamide, azlactone, polymethacrylate, and polystyrene.

8. The aborbent matrix of claim 1, wherein the unsubstituted native TNF-α is a human TNF-α and the single amino acid substitution is located in a first region of amino acids 29-36, a second region of amino acids 84-91, or a third region of amino acids 143-149.

9. The absorbent matrix of claim 1, wherein the plurality of TNF-α muteins immobilized on the extracorporeal biocompatible solid support have a lower binding activity to the soluble TNF receptor in the range of between about 5-fold to about 17-fold relative to the unsubstituted native TNF-α, and the plurality of TNF-α muteins immobilized on the extracorporeal biocompatible solid support have a lower cytotoxicity level in the range of between about 200-fold to about 12,500-fold relative to the unsubstituted native TNF-α.

10. The absorbent matrix of claim 1, wherein the soluble TNF receptor is soluble tumor necrosis factor receptor Type I (sTNFRI).

11. The absorbent matrix of claim 1, wherein the soluble TNF receptor is soluble tumor necrosis factor receptor Type II (sTNFRII).

12. The absorbent matrix of claim 1, wherein the TNF-α muteins immobilized on the extracorporeal biocompatible solid support is contained within a mixing chamber of the extracorporeal system.

13. The absorbent maxtrix of claim 1, wherein the plurality of TNF-α muteins further comprises-mutein 5 (SEQ ID NO:7), mutein 6 (SEQ ID NO:8), or combinations thereof.

* * * * *